(12) United States Patent
Gabriel et al.

(10) Patent No.: US 9,392,758 B2
(45) Date of Patent: Jul. 19, 2016

(54) TRANSFORMATION OF MATURE CITRUS

(75) Inventors: Dean W. Gabriel, Alachua, FL (US);
Giovana J. Perazzo-Ratto, Alachua, FL (US); Yingnan Jiang, Alachua, FL (US)

(73) Assignee: INTEGRATED PLANT GENETICS, INC., Gainesville, FL (US)

( * ) Notice: Subject to any disclaimer, the term of this patent is extended or adjusted under 35 U.S.C. 154(b) by 435 days.

(21) Appl. No.: 13/594,728

(22) Filed: Aug. 24, 2012

(65) Prior Publication Data
US 2013/0061349 A1 Mar. 7, 2013

Related U.S. Application Data

(60) Provisional application No. 61/527,995, filed on Aug. 26, 2011.

(51) Int. Cl.
*C12N 15/82* (2006.01)
*A01H 4/00* (2006.01)

(52) U.S. Cl.
CPC ............... *A01H 4/001* (2013.01); *A01H 4/005* (2013.01); *C12N 15/8202* (2013.01)

(58) Field of Classification Search
None
See application file for complete search history.

(56) References Cited

U.S. PATENT DOCUMENTS

| | | | |
|---|---|---|---|
| 6,103,955 A | 8/2000 | Pena-Garcia et al. | |
| 7,888,552 B2 * | 2/2011 | Ye et al. | 800/278 |
| 2006/0041956 A1 * | 2/2006 | Lassner et al. | 800/282 |
| 2007/0074314 A1 | 3/2007 | Ye et al. | |
| 2009/0300796 A1 | 12/2009 | Raemaekers et al. | |
| 2011/0119788 A1 | 5/2011 | Rodriguez Baixauli et al. | |

OTHER PUBLICATIONS

Dutt et al. Agrobacterium tumefaciens-mediated genetic transformation and plant regeneration from a complex tetraploid hybrid citrus rootstock, Scientia Horticulturae, vol. 123, pp. 454-458, Feb. 2010.*
Cervera et al. Production of transgenic adult plants from clementine mandarin by enhancing cell competence for transformation and regeneration, Tree Physiology 28, 55-66, © 2008 Heron Publishing-Victoria, Canada, Received Apr. 30, 2007; accepted Jun. 14, 2007; published online Oct. 15, 2007.*
Moore et al. Agrobacterium-mediated transformation of Citrus stem segments and regeneration of transgenic plants. Plant Cell Rep. 11(5-6):238-42. Jun. 1992.*
Dutt and Grosser (Evaluation of parameters affecting Agrobacterium-mediated transformation of citrus. Plant Cell Tiss Organ Cult. 98:331-340, 2009).*
Rolf Borchert et al., "Photoperiodic induction of synchronous flowering near the Equator", Nature, vol. 433, (2005).
Sandeepa Singh et al., "Citrus crop improvement through biotechnology Citrus biotechnology: Achievements, limitations and future directions", Mol. Biol. Plants 15(1), (2009).
Wilm Broolhearts et al., "Gene transfer to plants by diverse species of bacteria", Nature, vol. 433, (2005).
Antonio Weliton et al., "Agrobacterium of Citrus Sinesis and Citrus Iimonia Agrobacterium-Mediated Transformation of Citrus sinensis and Citrus Iimonia Epicotyl Segments", Scientia Agricola vol. 60, (2003).
European Extended Search Report for PCT/US2012/52452, mailed on Oct. 28, 2014.
International Search Report and Written Opinion based on International Patent Application No. PCT/US2012/052452, mailed on Jan. 28, 2013.
Cervera et al. "Agrobacterium-mediated transformation of citrange: factors affecting transformation and regeneration". 1998, *Plant Cell Rep.* 18:271-278, abstract only.
Cervera et al. "Genetic transformation and regeneration of mature tissues of woody fruit plants bypassing the juvenile stage", 1998, *Transgenic Research* 7:51-59, abstract only.
Almeida et al., "Genetic Transformation an d Plant Recovery from Mature Tissues of *Citrus sinensis* L. Osbeck.", 2003, Plant Science, 164(2):203-211, abstract only.
Broothaerts et al., "Gene transfer to plants by diverse species of bacteria.", 2005, *Nature*, 433(7026):629-33., abstract only.
Characterisation of regenerants obtained under selective conditions after Agrobacterium-mediated transformation of citrus explants reveals production of silenced and chimeric plants at unexpected high frequencies. Molecular Breeding 2004. 14:171-183.
Chinese Office Action and search report (English Translation) in application 201280052228.4, Issued Oct. 9, 2015.

* cited by examiner

*Primary Examiner* — Medina A Ibrahim
*Assistant Examiner* — Wayne Zhong
(74) *Attorney, Agent, or Firm* — Cooley LLP

(57) ABSTRACT

The invention relates to methods and compositions for genetic transformation of both juvenile and mature citrus. In some embodiments, the invention provides methods and compositions for genetic transformation of citrus using Rhizobia-mediated DNA delivery, and also methods of enhancing the frequency of genetic transformation of mature citrus by any DNA transfer method, including *Sinorhizobium*. Internodal stem sections prepared from epicotyls of citrus seedlings or freshly emerging shoots of mature citrus plants (e.g., first shoots from buds of mature plants following grafting onto rootstock or very young shoots of mature plants) are preconditioned for transformation by inducing callus formation on an artificial medium. All callus and any developing meristematic regions in immediately adjacent tissue are substantially or completely removed and the preconditioned explants are then transformed by *Sinorhizobium* or other known methods. Whole plants or shoots to be grafted onto rootstocks are subsequently regenerated from the transformed cells.

14 Claims, 8 Drawing Sheets pIPG973 (*A. tumefaciens*): 2/3 positive;
pIPG980 (*S. meliloti*): 3/5 positive

TRANSFORMATION OF MATURE CITRUS

CROSS REFERENCE TO RELATED APPLICATIONS

This application claims priority to U.S. Provisional Patent Application 61/527,995, filed on Aug. 26, 2011, which is herein incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing of the Sequence Listing (filename: INTE_007_01US_SeqList_ST25.txt, date recorded: Aug. 24, 2012, file size 52 kilobytes).

TECHNICAL FIELD OF THE INVENTION

The present invention relates to the field of plant biotechnology. In particular, the invention relates to methods for transforming woody plants. In some embodiments, the invention relates to pre-conditioning mature citrus to enable greatly increased transformation frequencies of mature citrus, thereby producing transgenic mature citrus plants, scions and citrus cells by using Rhizobiales species.

BACKGROUND OF THE INVENTION

All publications and patent applications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed inventions, or that any publication specifically or implicitly referenced is prior art.

Permanent genetic modification of plants requires the introduction of new genetic material into the genome of a plant cell, a process called transformation. Uniform, non-chimeric, permanent genetic modification of plants requires the introduction of new genetic material into the genome of a plant cell followed by the regeneration of an entire plant from that one cell. Uniform, non-chimeric, permanent genetic modification of plants can arise from the introduction of new genetic material into the nuclear genome, mitochondria or chloroplasts. Since there are multiple copies of the organelles in each cell, considerable additional care must be taken to ensure that all such organelles are direct descendants of the originally altered organelle. Most plant transformations are therefore designed to target the nuclear genome, and require integration of the new genetic material into a chromosome, where it becomes a new, permanent, gene locus.

To accomplish this, methods must be developed to introduce DNA past several physical barriers, specifically: the plant cell wall, the cell membrane and the nuclear envelope. The plant cell wall deserves particular mention because unlike animal cell walls, which have extremely thin walls, plant cell walls form an extremely thick (ca. 20 nanometers), rigid structure comprised of cellulose fibrils encased in a cement of polysaccharide and proteins. Plant transformation therefore requires specialized methods for plant cell wall penetration that differ from those used for animal cell transformation, which typically involves direct DNA transfer methods.

SUMMARY OF THE INVENTION

The present invention provides methods for transforming woody plants. In some embodiments, the present invention provides methods for transforming *Citrus* species plants. In some embodiments, the *Citrus* species plant is a juvenile plant or a mature plant. In some embodiments, the methods comprising a tissue preconditioning step. In some embodiments, the transformation is a direct transformation, for example, DNA-coated microprojectile bombardment, or other known direct transformation methods. In some embodiments, the transformation is an indirect transformation, for example, microorganism-mediated transformation. In some embodiments, the indirect transformation is mediated by the species in the Rhizobiaceae family. In some embodiments, the species in the Rhizobiaceae family is an *Agrobacterium* species. In some embodiments, the *Agrobacterium* species is *Agrobacterium tumefaciens*. In some other embodiments, the species in the Rhizobiaceae family is a non-*Agrobacterium* microorganism. In some embodiment, the non-*Agrobacterium* microorganism is a *Sinorhizobium* species. In some embodiments, the *Sinorhizobium* species is *Sinorhizobium meliloti*.

The present inventors have discovered a tissue preconditioning method that greatly enhances transformation of both juvenile and mature citrus using at least either *Agrobacterium* or non-*Agrobacterium* indirect transformation methods. In one embodiment of the invention, *Sinorhizobium meliloti* is used for transformation of juvenile and mature citrus. In another embodiment of the invention, *Agrobacterium tumefaciens* is used for transformation of juvenile and mature citrus. Other indirect methods of transformation using other bacteria in the Rhizobiaceae may be used by those skilled in the art, and other direct methods of plant cell transformation may be used by those skilled in the art, such as DNA-coated microprojectile bombardment, or ether known transformation methods.

In some embodiments where *Sinorhizobium meliloti* is used for transformation of juvenile and mature citrus, the resulting percentage of transformed shoots based on tolerance to a selection agent (e.g., shoot growth on kanamycin) is about 13% to about 21%, about 10% to about 30%, or about 0.8% to about 12.6%. In other embodiments where *Sinorhizobium meliloti* is used for transformation of juvenile and mature citrus, the resulting percentage of transformed shoots with tolerance to a selection agent (e.g., shoot growth on kanamycin) ranges from about 0.1% to 50%; and, in some embodiments is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, or about 50%.

In some embodiments where *Agrobacterium tumefaciens* is used for transformation of juvenile and mature citrus, the resulting percentage of transformed shoots with tolerance to a selection agent (e.g., shoot growth on kanamycin) is about 4% to about 16%, or to about 17%. In other embodiments where *Agrobacterium tumefaciens* is used for transformation of juvenile and mature citrus, the resulting percentage of transformed shoots with tolerance to a selection agent (e.g., shoot growth on kanamycin) ranges from about 0.1% to about 50%; and, in some embodiments is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, or about 50%.

In certain embodiments, the percentage of rooting shoots (i.e., shoots that produce roots) after transformation with *Sinorhizobium meliloti* or *Agrobacterium tumefaciens* is about 2% to about 5%, about 1.5% to about 5%, or about 2.7% to about 3.6%. In other embodiments, the percentage of rooting shoots after transformation with *Sinorhizobium meliloti* or *Agrobacterium tumefaciens* ranges from about 0.1% to about 20%; and, in some embodiments is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In certain embodiments, the percentage of transgenic grafted shoots after transformation with *Sinorhizobium meliloti* or *Agrobacterium tumefaciens* is about 0.3% to about 6%, or about 0.25% to about 3.5%. In other embodiments, the percentage of grafted shoots after transformation with *Sinorhizobium meliloti* or *Agrobacterium tumefaciens* ranges from about 0.1% to about 20%; and, in some embodiments is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

In some embodiments, the preconditioning step comprises inducing callus formation from stem sections of a citrus plant on a medium. In some embodiments, the stem sections are the internodal stem sections prepared from epicotyls of freshly emerging shoots of mature citrus plants (e.g., first shoots from buds of mature plants following grafting onto rootstock or very young shoots of mature plants). In some embodiments, the preconditioning step further comprises removing at least 70%, at least 80%, at least 90%, at least 99%, or 100% callus and any developing meristematic regions in immediately adjacent tissue. The preconditioned explants are then transformed by *Sinorhizobium* or other known methods. After transformation, the multiple shoot cultures may be transferred to a selection medium to differentiate transformed and non-transformed cells. Whole citrus plants or shoots to be grafted onto rootstocks are subsequently regenerated from the transformed cells. The present invention provides certain advantages over existing methods because it can be used to transform mature citrus, which is normally recalcitrant to transformation even at moderate efficiencies.

In some embodiments, the present invention provides methods of producing a transformed juvenile or mature plant, comprising: (a) culturing a non-meristematic citrus tissue recalcitrant for transformation on a culture medium to produce callus tissue; and (b) removal of the callus tissue and all meristematic tissue. In some embodiments, the methods further comprise (c) introducing a nucleic acid into a cell of the now preconditioned tissue, thereby producing a transformed cell comprising the nucleic acid; and (d) regenerating a transformed plant from the transformed cell. The tissue can be an internodal stem section excised from a the first shoots from buds of mature citrus plants following grafting onto rootstock, very young shoots of mature plants or an internodal epicotyl from a juvenile seedling. In some embodiments, the mature citrus is a commercially valuable sweet orange, such as 'Hamlin', 'Valencia' or 'Mid-Sweet'. In some embodiments, the juvenile citrus is a rootstock, such as 'Carrizo'.

In some embodiments, the preconditioning culture medium comprises at least one plant growth regulator, for example, a cytokinin. In another embodiments, the growth regulator is selected from the group consisting of 6-furfurylaminopurine (kinetin), 6-benzyl-aminopurine (6-BAP), 6-dimethyallylamino-purine (2ip), trans-6-(4-hydroxzy-3-methlbut-2-enyl)amino-urine (zeatin), TDZ, gibberellic acid (GA), IAA, NAA, dicamba, 2,3,5-T and 2,4-D, and functional derivatives thereof. The concentration of growth regulator in the culture medium is between about 0.01 mg/L to about 25 mg/L, for example, about 0.02 mg/L, about 0.04 mg/L, about 0.06 mg/L, about 0.07 mg/L, about 0.1 mg/L, about 0.2 mg/L, about 0.4 mg/L, about 0.6 mg/L, about 0.8 mg/L, about 1.0 mg/L, about 2.0 mg/L, about 4.0 mg/L, about 6.0 mg/L, about 8.0 mg/L, about 10.0 mg/L, about 12.0 mg/L, about 14.0 mg/L, about 16.0 mg/L, about 18.0 mg/L, about 20.0 mg/L, about 22.0 mg/L, or about 25.0 mg/L. In some embodiments, the concentration of growth regulator in the culture medium is between about 0.01 mg/L to about 10 mg/L, between about 0.01 mg/L to about 5 mg/L, or between about 0.05 mg/L to about 8 mg/L. In some embodiments, the nucleic acid is introduced into the cell by microparticle bombardment, electrophoresis or electroporation, or using a bacterium belonging to the family Rhizobiaceae. In some embodiments, the nucleic acid comprises a nucleic acid that is heterologous to the dicotyledonous plant. In some embodiments, the nucleic acid comprises a selection marker gene, for example, gene that encodes a neomycin phosphotransferase (nptII) activity, or a gene that encodes a polypeptide having GUS activity. In some embodiments, the nucleic acid is a vector comprising a nucleic acid comprising a gene heterologous to the plant.

In yet some other embodiments, step (c) of the method comprises: selecting a shoot comprising a transformed mature citrus cell; growing the shoot under conditions that promote shoot elongation to produce at least one transformed mature citrus shoot; and then growing the at least one transformed shoot into a mature transformed plant. For example, the at least one transformed shoot grows into a mature transformed plant after grafting growing the at least one transformed shoot onto a rootstock. In some embodiments, the rootstock is grown from seeds.

In yet some other embodiments, step (c) of the method comprises: selecting a shoot comprising a transformed juvenile citrus cell; growing the shoot under conditions that promote shoot elongation to produce at least one transformed juvenile citrus shoot; and then growing the at least one transformed shoot into a transformed plant. In some embodiments, the at least one transformed shoot grows into a transformed plant after growing the at least one transformed shoot on a medium that promotes root formation.

In yet some other embodiments, step (c) of the method comprises: selecting a shoot comprising a transformed juvenile or mature citrus cell; growing the culture under conditions that promote shoot elongation to produce at least one transformed shoot; cloning the at least one transformed juvenile or mature citrus shoot; and then growing the at least one transformed shoot into juvenile or mature transformed plants, either by grafting the clones onto transformed or nontransformed rootstocks, or by growing the clones on a medium that promotes root formation.

The present invention further provides a transformed citrus plant part or plant cell produced by any one of the methods above; and a transformed plant produced by any one of the methods above. In some embodiments, the transformed plant is mature sweet orange or a juvenile rootstock that expresses a polypeptide of interest. In some embodiments, the transformed plant is a citrus plant that expresses a polypeptide having anti-bacterial activity. The present invention further provides a seed produced by a transformed plant above, wherein the seed comprises the nucleic acid transformed into the citrus plant cell culture and a plant grown from the seed.

The present invention further provides methods of producing a citrus plant comprising a transformed plastid genome, comprising: (a) culturing a non-meristematic citrus tissue recalcitrant for transformation on a culture medium to produce callus tissue; and (b) removal of the callus tissue and all meristematic tissue. In some embodiments, the methods further comprise (c) introducing a nucleic acid into a plastid genome of a cell of the now preconditioned tissue, thereby producing a transformed cell comprising the nucleic acid; and (d) regenerating a transformed plant from the transformed cell. In some embodiments, the transformed cell is homoplasmic for transformed plastid genomes. In some embodiments, the plant is homoplasmic for transformed plastid genomes.

In some embodiments, the plant is a woody dicotyledonous plant. For example, the plant is a member of the Rutaceae family. In some embodiments, the culture medium comprises at least one plant growth regulator, such as a cytokinin. In some embodiments, the growth regulator is selected from the group consisting of 6-furfurylaminopurine (kinetin), 6-benzyl-aminopurine (6-BAP), 6-dimethyallylamino-purine (2ip), trans-6-(4-hydroxzy-3-methlbut-2-enyl)amino-urine (zeatin), TDZ, gibberellic acid (GA), IAA, NAA, dicamba, 2,3,5-T and 2,4-D. In some embodiments, the concentration of growth regulator in the culture medium is between about 0.01 mg/L to about 25 mg/L, for example, about 0.02 mg/L, about 0.04 mg/L, about 0.06 mg/L, about 0.07 mg/L, about 0.1 mg/L, about 0.2 mg/L, about 0.4 mg/L, about 0.6 mg/L, about 0.8 mg/L, about 1.0 mg/L, about 2.0 mg/L, about 4.0 mg/L, about 6.0 mg/L, about 8.0 mg/L, about 10.0 mg/L, about 12.0 mg/L, about 14.0 mg/L, about 16.0 mg/L, about 18.0 mg/L, about 20.0 mg/L, about 22.0 mg/L, or about 25.0 mg/L. In some embodiments, the concentration of growth regulator in the culture medium is between about 0.01 mg/L to about 10 mg/L, about 0.01 mg/L to about 5 mg/L, or about 0.05 mg/L to about 8 mg/L. The nucleic acid can be introduced into the cell by microparticle bombardment, electrophoresis or electroporation. In some embodiments, the nucleic acid comprises a nucleic acid that is heterologous to the dicotyledonous plant. For example, the nucleic acid is a vector comprising a nucleic acid comprising a gene heterologous to the dicotyledonous plant.

In one aspect, the invention provides methods for transforming a citrus plant cell, comprising: (a) contacting at least a first plant cell with a bacterium other than *Agrobacterium* sp. comprising: (i) a first nucleic acid comprising a vir gene region of a Ti plasmid wherein the vir gene region acts to introduce a nucleic acid coding for a sequence of interest into the plant cell in a VirD2-dependent manner; and (ii) a second nucleic acid comprising one or more T-DNA border sequence(s) operably linked to a nucleic acid of interest; and (b) selecting at least a first plant cell transformed with the nucleic acid of interest, wherein the plant cell is a citrus plant cell.

In some embodiments of the invention, the bacterium may be a Rhizobia cell. In certain embodiments, the Rhizobia are grown under suitable conditions to minimize polysaccharide production by the Rhizobia cells. The Rhizobia cell may be grown in the presence of acetosyringone or other compound, such as a phenolic compound, that induces vir gene function prior to contacting the plant cell. The Rhizobia cell may be selected from the group consisting of: *Rhizobium* spp., *Sinorhizobium* spp., *Ensifer* spp., *Mesorhizobium* spp., *Phyllobacterium* spp. *Ochrobactrum* spp. and *Bradyrhizobium* spp. In specific embodiments, the Rhizobia cell is a *Sinorhizobium meliloti*.

In another aspect of transformation methods provided by the invention, a plant cell that is transformed may be comprised in an explant from a citrus seed, for example, from a seedling, callus, cell suspension, cotyledon, epicotyls, meristem, or shoot. The explant may comprise an embryonic meristem explant; callus; cell suspension; cotyledon; or tissue from leaves, roots, or stems.

In another aspect of transformation methods provided by the invention, a plant cell that is transformed by be comprised of an explant from emerging shoots of mature citrus plants. The explant may comprise non-embryonic internodal stem sections prepared from epicotyls of citrus seedlings or freshly emerging shoots of mature citrus plants (e.g., first shoots from buds of mature plants following grafting onto rootstock or very young shoots of mature plants). The explant may comprise non-embryonic internodal stem sections in which all meristematic tissue is removed.

A bacterium used for transformation in accordance with the invention may comprise nucleic acids introduced, for example, by electroporation or conjugation. The sequences may comprise nucleic acid required for conjugative transfer independent of VirD2 function. The nucleic acids may include first and second nucleic acids.

In another aspect of the invention, transformation methods provided herein may comprise selecting a plant cell transformed with a nucleic acid of interest in the absence of a selection agent. Selecting a plant cell transformed with a nucleic acid of interest may comprise culturing the plant cell in the presence of a selection agent, wherein the nucleic acid of interest confers tolerance to the selection agent or is operably linked to a further nucleic acid that confers tolerance to the selection agent, for example, kanamycin. In some embodiments, the nucleic acid of interest contains a selectable, screenable, or scoreable marker gene. These genetic components are also referred to herein as functional genetic components, as they produce a product that serves a function in the identification of a transformed plant, or a product of agronomic utility. The DNA that serves as a selection or screening device may function in a regenerable plant tissue to produce a compound that would confer upon the plant tissue resistance to an otherwise toxic compound. A number of screenable or selectable marker genes are known in the art and can be used in the present invention. Examples of selectable markers and genes providing resistance against them are disclosed in Miki and McHugh, 2004. Genes of interest for use as a selectable, screenable, or scoreable marker would include but are not limited to gus, gfp (green fluorescent protein), luciferase (LUX), genes conferring tolerance to antibiotics like kanamycin, neomycin, kanamycin, paromomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase, genes that encode enzymes that give tolerance to herbicides like glyphosate (e.g. 5-enolpyruvylshikimate-3-phosphate synthase (EPSPS). Other selection procedures can also be implemented including positive selection mechanisms (e.g. use of the manA gene of *E. coli*, allowing growth in the presence of mannose) and would still fall within the scope of the present invention (see also Miki and McHugh (2004)). In yet other embodiments, the nucleic acid of interest may be defined as not physically linked to a selectable marker gene. For example, the marker gene and nucleic acid of interest may genetically segregate in progeny of a plant regenerated from the plant cell transformed with the nucleic acid of interest.

A bacterium in accordance with the invention may comprise at least a third nucleic acid comprising a further nucleic acid of interest, wherein the citrus plant cell is transformed with the third nucleic acid. In some embodiments of the invention, a citrus plant may be regenerated from a transgenic citrus plant cell, wherein the citrus plant comprises the sequence of interest. Regenerating a citrus plant may comprise inducing formation of one or more shoots from an explant comprising the plant cell and cultivating at least a first shoot into a whole fertile plant by inducing formation of roots or by grafting at least a first shoot onto a transgenic or nontransgenic rootstock, wherein a graft union is formed and the grafted shoot comprises a nucleic acid of interest. In certain embodiments, the rootstock may be grown from citrus seeds. In further embodiments, the rootstock may be grown from tissue culture and transferred to soil. In further embodiments, the grafted shoot and graft union are protected from desiccation, insects, microbes and other environmental insults by a plastic covering.

In another aspect, the invention provides a Rhizobia cell selected from the group consisting of: *Rhizobium* spp., *Sinorhizobium* spp., *Ensifer* spp., *Mesorhizobium* spp., *Phyllobacterium* spp. *Ochrobactrum* spp. and *Bradyrhizobium* spp., the cell comprising (i) a first nucleic acid comprising a vir gene region of a Ti plasmid wherein the vir gene region acts to introduce a nucleic acid coding for a sequence of interest into a plant cell in a VirD2-dependent manner; and (ii) a second nucleic acid comprising one or more T-DNA border sequence(s) operably linked to a nucleic acid coding for a sequence of interest. In one embodiment, the cell is further defined as comprising a selectable marker. In another embodiment, the Rhizobia cell is *Sinorhizobium meliloti* cell.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
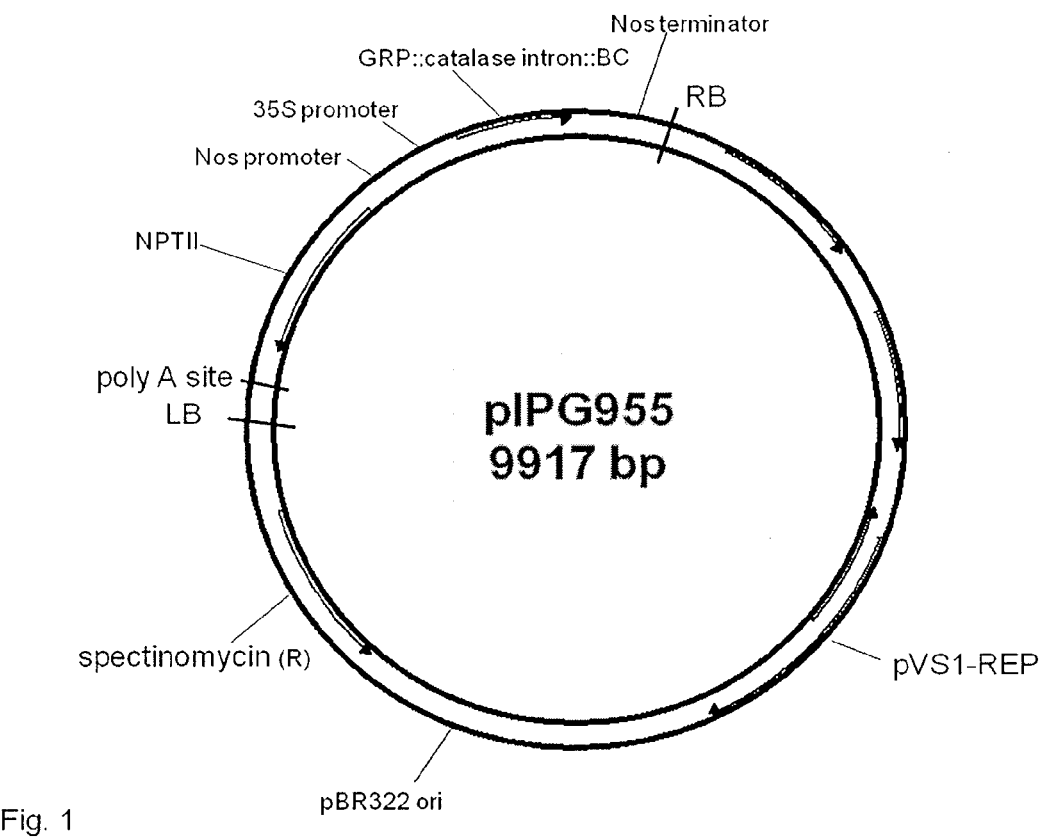
FIG. 1: Schematic map of pIPG955. LB, Left T-DNA border; RB, Right T-DNA border.

The following is a detailed description of the invention provided to aid those skilled in the art in practicing the present invention. Those of ordinary skill in the art may make modifications and variations in the embodiments described herein without departing from the spirit or scope of the present invention.

Plant Transformation Methods

Several direct plant transformation methods using DNA have been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). This technique has almost exclusively been done using plant cells treated with enzymes to partially or fully remove the thick cell walls, forming protoplasts. There are a few exceptions (Lee et al., 1989; Chowrira et al. 1998), but these did not result in the regeneration of fully transgenic plants. Use of sonication was reported as yet another method to provide direct transformation of plant protoplasts (Joersbo et al. 1990). This method suffers, as do the others requiring use of protoplasts, by the tedious process required to create and preserve plant protoplasts and then regenerate them into whole plants following transformation. Protoplast formation and regeneration is tedious and technically demanding, even in the best of circumstances (Potrykus, 1990) and impossible with many plant species. Even if the tissue is regenerable, often the resulting plants are non-fertile.

A second direct transformation method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. No. 5,204,253, U.S. Pat. No. 5,015, 580). The method used requires both specialized equipment and expensive reagents. A more serious problem with this method is that each particle that enters a particular cell is usually coated with multiple copies of the DNA provided for transformation, thereby usually resulting in multiple DNA insertions (Pederson et al., 1997; Kohli et al., 1998; Pawlowski & Somers, 1998; Jackson et al., 2001). Multiple insertions frequently lead to gene silencing and the greater the number of insertions, the lower the gene expression level (Stoger et al., 1998; Popelka et al., 2003). In order to make this method work for practical purposes requires a tedious attention to a combination of factors that must be optimized. These include: genotype specific tissue culture (Shimada, 1978) and transformation response (Iser et al., 1999; Rasco-Gaunt et al., 2001), quality and developmental stage of the explants at the time of culture initiation (Armaleo et al., 1990), culture medium composition (Barro et al., 1998) and culture conditions, culture period before and after biolistic gene transfer (Rasco-Gaunt et al., 1999), osmotic treatment of the tissue cultures to reduce tissue damage during biolistic gene transfer (Vain et al., 1993), transgene expression cassettes (Li et al., 1997), biolistic gene transfer system and its specific parameters (Altpeter et al., 1996) and the selection system and its parameters (Christou & Ford, 1995). Clearly, better methods are required.

*Agrobacterium*-mediated plant transformation involves as a first step the placement of DNA fragments cloned on plasmids into living *Agrobacterium* cells, which are then used to "infect" individual living plant cells. This process is therefore an indirect transformation method, is well known in the art, and when it works, typically results in relatively stable transferred DNA (T-DNA) insertions in plants (Park et al. 2004), stable expression of the inserted gene, frequent recovery of plants exhibiting a normal phenotype (Vidal et al., 2003), and single insertion events are frequently observed after gene delivery (Cheng et al., 1997; Fang et al., 2002). The *Agrobacterium* infection process requires attachment to the host plant cell, which involves a highly specific attachment process that is an essential part of what determines the host range specificity of the bacterium. Attachment to plant cells is necessary for transformation and is mediated by chromosomally encoded *Agrobacterium* genes (Lippincott and Lippincott, 1969; Douglas et al, 1982).

Host range can also be determined by a second, independent process involving Vir gene activation, but Vir gene activation can be artificially accomplished by chemical induction using acetosyringone (Pitzschkel & Hirt, 2010 and references therein). The Vir genes of *Agrobacterium* are located on a 200 kb plasmid called the tumor inducing (Ti) plasmid, which also encodes functions for Ti plasmid transfer between bacterial strains and species and the initiation, processing and transfer into the plant nucleus of the T-DNA, which in natural wild type strains encodes "oncogenes" that when expressed in plant cells, cause tumors (Wood et al., 2001). The T-DNA is delimited by two border regions, referred to as right border (RB) and left border (LB). For plant transformation purposes, the natural T-DNA is modified by removal of the tumor-inducing genes lying within the RB and LB (such Ti plasmids are "disarmed"), and replacement with genes of interest. The T-DNA may be located on a separate plasmid vector from the large plasmid carrying the Vir genes for convenience in DNA cloning; such systems are called T-DNA binary vector systems.

Activation of the Vir genes in *Agrobacterium* causes formation of the Type 4 secretion machine, which can transfer both virulence proteins and DNA attached to virulence protein from the bacterium, through the plant cell wall, into the plant cytoplasm, into the nucleus, and ultimately, integrated into the nuclear DNA at random sites. Activation of the VirD2 gene in particular causes the transfer of T-DNA. All DNA located between the two borders is transferred into plant cell. Plasmids carrying VirD2 functions by nicking the T-DNA to produce single stranded transfer DNA (the "T-strand") with VirD2 covalently attached to the 5' end of the T-strand. A second Vir protein, encoded by the VirE2 gene, wraps around the T-DNA, and the entire protein-DNA complex is transferred into the plant cell. Both the VirE2 and VirD2 proteins encode nuclear localization signal (NLS) sequences and after transfer into the plant cytoplasm, these NLS signals serve to guide the complex to the plant cell nucleus, where the T-strand is integrated in the plant genome with the help of both *Agrobacterium* virulence proteins and plant factors.

*Agrobacterium* thus breaches all three physical barriers: thick cell wall, cell membrane and nuclear envelope, to introduce the DNA, and the process is well documented. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. No. 5,693,512, U.S. Pat. No. 6,051,757 and EP904362A1. These references exemplify the wide, but not unlimited, host range of *Agrobacterium*, and is a primary reason for its widespread use.

However, *Agrobacterium* transformation of monocots, including corn, rice, wheat, barley and sugarcane is generally very difficult because monocots are not natural hosts; infection of many nonhost dicot species is similarly extremely low and highly genotype dependent (Lee et al., 2004). For example, cotton transformation by *Agrobacterium* has been largely limited to tetraploid Coker cultivars or closely related genotypes (Gould and Megallus-cedeno, 1997; Zapata et al, 1999; Satyavathi et al 2002; Kategari et al 2007). Transformation of other tetraploid cultivars or of diploid or indigenous cotton cultivars has not been reported to date using any method. In addition, *Agrobacterium* infects some plant tissues much more efficiently than others. As a result, most of the patents covering use of *Agrobacterium* are directed to very particular ways to obtain the transformation of specific tissues, including embryo tissue, callus tissue, pollen, apical meristems, floral parts, seeds and other living plant parts. For example, in the above cited cotton examples, only shoot-tip transformation methods were used. As a further example, Zhong et al. (2005) claim use of *Agrobacterium* or particle bombardment to transform multiple shoot structures induced in cultures from meristematic tissues of difficult to transform species of squash, melon, watermelon, or sunflower (U.S. Pat. No. 6,858,777). There is no teaching or suggestion of the use of non-*Agrobacterium* cells with such tissues.

When *Agrobacterium* infections of nonhosts occur or are forced, the frequency is nearly always much lower than on hosts. In some cases, methods to force such infections are unknown. This points to a need and often, a necessity, for development of more efficient plant transformation methods using non-*Agrobacterium* methods.

A more recently described indirect plant transformation method used living members of a non-*Agrobacterium* group of plant associated bacteria collectively called Rhizobia (Broothaerts et al., 2005, U.S. Patent Application Publications 20050289667; 20050289672; U.S. Pat. No. 7,888,552 and references therein). Rhizobia are in the same bacterial family as *Agrobacterium*, the Rhizobiales, and include *Rhizobium* spp., *Sinorhizobium* spp., *Ensifer* spp., *Mesorhizobium* spp., *Phyllobacterium* spp., *Ochrobactrum* spp., and *Bradyrhizobium* spp. Different Rhizobia exhibit wide genomic diversity, and there is little doubt that *Agrobacterium* and *Sinorhizobium* are in distinctly different phylogenetic clades (Galibert, F. et al. 2001; Wood et al., 2001). Importantly, different Rhizobia also exhibit significantly different host ranges, and respond to different host-specific molecular signals (Long, 2001). Weller et al. (2004, 2005) reported that several Rhizobia, including strains of *Rhizobium* sp. and *Ochrobactrum* sp. that harbored root inducing (Ri) plasmids, but not Ti plasmids, transferred DNA into (i.e., transformed) cucumber and tomato plants, leading to "hairy root" disease.

Taxonomic assignment may be done as is known in the art, for instance by comparison of 16S rDNA sequences or other classification methods. Wild type strains of many Rhizobia species are typically able to induce formation of nitrogen fixing nodules in root tissues of host plants such as leguminous plants (Fabaceae). However, the ability to nodulate roots of a given plant species is not required for *Rhizobium*-mediated DNA transfer into cells of the plant species.

Broothaerts et al., (2005) reported transformation by *Rhizobium* sp., *Mesorhizobium loti*, and *Sinorhizobium meliloti* strains using a binary Ti plasmid transformation system that was added to the native Rhizobia strains. Transformation was limited to *Arabidopsis*, tobacco, and rice. More recently, Ye et al (U.S. Pat. No. 7,888,552) demonstrated use of *Rhizobium* sp., *Sinorhizobium* sp., and *Mesorhizobium* sp. to transform species that were difficult to transform with *Agrobacterium*. This patent was limited to soybean, canola, corn, and tetraploid cultivar Coker cotton cells. More recently, Wendt et al. (2011) demonstrated use of *Rhizobium* sp., *Mesorhizobium loti*, and *Sinorhizobium meliloti* to transform potato. Both Broothaerts et al. (2005) and Went et al. (2011) reported that strain-specific optimizations were necessary for using Rhizobia strains to transform plant tissues.

Transformation of juvenile citrus using *Agrobacterium* has been hampered by low transformation efficiencies and transformation of commercial varieties of mature citrus using *Agrobacterium* is so rare as to be practically useless. Transfer of DNA to citrus cells by non-*Agrobacterium* bacterial strains has not been reported. There is, therefore, a great need in the art for the development of improved methods allowing the transformation of commercially important citrus crop varieties such as 'Hamlin' and 'Valencia' using any means, including non-*Agrobacterium* bacterial strains, and improving transformation efficiencies of mature citrus and citrus in general. Additional citrus crop species that may be transformed by the present invention include *Citrus sinensis, Citrus aurantium, Citrus paradisi, Citrus limon, Citrus aurantiifolia, Citrus maxima, Citrus medica, Citrus reticulata, Citrus trifoliata*, Kumquats, Papedas, Australian limes, and the various hybrids, varieties, sports, and cultivars of these species.

The method(s) used must not introduce mutations in the donor or transforming DNA nor the recipient DNA. The genetic alteration must be stably inherited by progeny of the transformed plant. Progeny can then be obtained either asexually, by taking multiple cuttings of the transformed plant, or sexually, through seed. The preferred method for plant propagation depends on the species; for example, fruit-producing citrus trees are nearly always propagated asexually, although the rootstocks are nearly always produced from seeds.

Some plants commonly reproduce asexually through seed by a process called apomixis (Nogler, 1984). Apomixis gives rise to fertile seeds in which the embryos derive entirely from maternal cells rather than from the fusion of male and female gametes to form a zygote. Therefore, apomictic embryos have a genetic constitution identical to that of the female parent. Many members of the genus *Citrus* and some closely related genera belonging to Rutaceae reproduce primarily apomictically by nucellar embryony (Frost 1943). Since nucellar embryos develop asexually by ordinary mitotic division of cells of the nucellus and the male gamete does not contribute to their formation, nucellar seedlings are identical to the maternal seed parent. Indeed, propagation of citrus rootstocks depends upon the production of clonal plants from nucellar seedlings, making apomixis one of the most important and highly conserved traits in breeding programs for citrus rootstocks (Garcia, R. 1999).

The only time that citrus seeds are used commercially is in the production of rootstocks, and then only from specialized nursery operations with registered rootstock "mother trees".

'Carrizo' citrange is a favored rootstock that is highly apomictic; zygotic embryos from 'Carrizo' (i.e., those developing from a genetic cross) are very rare ('Swingle', 1927). Even with a rootstock that exhibits a relatively high (5% to 10%) proportion of zygotic embryos, such as 'Swingle' citrumelo, most zygotic embryos arise via. self-fertilization and not from cross-pollination, likely because of differences in the timing of flowering among various cultivars (Anderson et al., 1991). Overall, cultural practices in rootstock production and selection of the apomixis trait by rootstock breeders combine to make rootstock outcrossing exceedingly rare. Rootstock operations take care to eliminate any seedlings that appear to be offtype (and which may have arisen from self-fertilization, or very rarely, cross pollination; Anderson et al., 1991).

By contrast with rootstock production, the fruit producing portion of a citrus tree scion is never propagated commercially by seed, in part because the seedlings will not flower (and therefore will not produce fruit) until they break juvenility, a process that takes many years. After flowering, the tissue is said to be "mature". The maturation process takes anywhere from five to twelve years, depending on variety, and this is true of both zygotic and nucellar seedlings (Clark, 1983; Spiegel-Roy and Goldschmidt, 1996). Therefore instead of growing fruit producing varieties from seed, commercial producers of citrus always graft mature "budwood", called the scion, onto juvenile rootstocks, and the mature budwood will then flower the first year after grafting. That is, all commercial citrus scions are propagated vegetatively (i.e., asexually), and therefore all have a genetic constitution identical to that of the parent. This includes the edible fleshy fruit and rind, which also has a genetic constitution identical to that of the parent. Only the seeds of such fruit have a possibility of genetic outcrossing, and then only to the extent that the variety is zygotic and not apopmictic (refer next paragraph). Any citrus seeds that may be produced in such fruit are quite useless for propagation purposes, because even if germinated, the seedlings will be juvenile and remain so for years.

Juvenile citrus tissue transformation using *Agrobacterium* has been achieved (Moore et al., 1987; Cervera, 1998), although frequencies are low to moderate, depending upon the citrus variety. The primary problem with transformation of juvenile citrus, however, is that transformed trees will not flower until juvenility is broken. This makes it impossible to evaluate transgenic trees for fruit quality, quantity, and general horticultural performance for up to 12 years, depending on variety. Transformation of mature citrus is one potential answer to the problem. However, although transformation of some cultivars of juvenile citrus by current methods using *Agrobacterium* is at low-moderate frequency, transformation of mature citrus is extremely difficult, with only two groups (in Spain and Brazil) having reported it, and without frequency data (Cervera et al., 1998, 2008; Almeida et al., 2003; Pena-Garcia et al., U.S. Pat. No. 6,103,955). Prior to the present invention, as far as the inventors know, transformation of mature citrus using *Agrobacterium* remains commercially impractical, and transformation of citrus using any other transformation method has not been reported. The methods of Pena-Garcia et al (U.S. Pat. No. 6,103,955) require the steps of in vitro micrografting of transformed mature citrus onto citrus stocks cultivated in vitro, followed by the additional step of grafting the resulting in vitro micrografted plants onto other citrus stocks or transplanting the in vitro grown plants into soil for hardening off. Micrografting of transformed mature citrus directly onto citrus stocks rooted in soil as disclosed herein saves a tedious and time-consuming step and results in much more rapid growth of the transformed tree, and was not anticipated or specified in U.S. Pat. No. 6,103, 955.

DEFINITIONS

The following definitions are provided in order to aid those skilled in the art in understanding the detailed description of the present invention.

"Selectable marker" or "screenable marker" refers to a nucleic acid sequence whose expression confers a phenotype facilitating identification of cells, tissues, or plants containing the nucleic acid sequence.

"Transcription" refers to the process of producing an RNA copy from a DNA template.

"Transformation" refers to a process of introducing an exogenous nucleic acid sequence into a cell or tissue. The transformation may be transient or stable. In stable transformations, part or all of the exogenous nucleic acid is incorporated (e.g., integrated or stably maintained) in the nuclear genomic DNA, plastid DNA, or is capable of autonomous replication in the nucleus or plastid.

"Transgenic" refers to organisms into which an exogenous nucleic acid sequence has been stably transformed.

As used herein, the verb "comprise" as is used in this description and in the claims and its conjugations are used in its non-limiting sense to mean that items following the word are included, but items not specifically mentioned are not excluded.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots". "Freshly emerging shoots" are shoots that have appeared as new growth on a plant in about the last 1 day, 2 days, 3 days, 4 days, 5 days, 6 days, 1 week, 2 weeks, 3 weeks, or 4 weeks.

As used herein, the term "plant tissue" refers to any part of a plant. Examples of plant organs from which plant tissue may be derived include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

A plant stem is generally divided into nodes and internodes. The nodes hold buds which grow into one or more leaves, inflorescence (flowers), roots, other stems, etc. The internodes distance one node from another. An "internodal stem section" refers to a cut segment of an internode.

An "epicotyl" is the embryonic shoot above the cotyledons. Generally, the epicotyl will develop into the leaves of the plant. The cotyledons are parts of the embryo within the seed of a plant that, upon germination, may become the embryonic first leaves of a seedling.

A "graft" is produced by connecting two pieces of living plant issue together so that they will unite and form a functional plant and subsequently grow as one new plant. The "scion" is the aerial part of a plant that forms the crown of the new plant. The "rootstock" is the belowground or lower part of a plant, sometimes including part of the stem and some branches that will form the root system of the new plant. The "graft union" is the place on the stem of a plant where the scion is joined to the rootstock. The scion tissue that is grafted onto a rootstock may comprise a stem section of approximately the same diameter as that of the rootstock stem section and include leaves, or may be much smaller, as in the case of "budwood". Budwood is the mid-part of a one-year old shoot from a desired scion variety, used to furnish an axillary bud for grafting. The axillary bud is an embryonic shoot which lies at the junction of the stem and petiole of a plant. Such axillary buds, derived from a scion and grafted onto a rootstock, will generate nearly the entire above ground part of the tree, except for the portion of the stem of the rootstock that is above ground. After the grafted scion forms stems and leaves that can photosynthetically support the growth of the roots, all shoots from the rootstock are typically removed. Most citrus trees grown today consist of a scion variety grafted from budwood to a rootstock. After a graft, the "first flushes" are the newest stems and leaves that emerge from the graft, including grafts from axillary buds.

As used herein, the phrase "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

In some embodiments, the present invention provides varieties derived from the plants produced by the compositions, methods, and systems described herein. As used herein, the term "variety" refers to a subdivision of a species, consisting of a group of individuals within the species that are distinct in form or function from other similar arrays of individuals.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

In some embodiments, the present invention provides genotypes derived from the plants produced by the compositions, methods, and systems described herein. As used herein, the term "genotype" refers to the genetic makeup of an individual cell, cell culture, tissue, organism (e.g., a plant), or group of organisms.

In some embodiments, the present invention provides clones derived from the plants produced by the compositions, methods, and systems described herein. As used herein, the term "clone" refers to a cell, group of cells, a part, tissue, organism (e.g., a plant), or group of organisms that is descended or derived from and genetically identical or substantially identical to a single precursor. In some embodiments, the clone is produced in a process comprising at least one asexual step.

An "explant" or "mother plant" is the source of cells to be developed during the tissue culturing process. For example, the explant can be any segment or collection of cells from apical meristems, terminal buds, axillary buds, adventitious buds, accessory buds, pseudo-terminal buds, cambium, lateral meristem, lateral bud, vegetative buds, reproductive buds, mixed buds, shoot segments, shoot apices, stem segments, immature nodal sections from stems, lateral shoots, seedlings, seeds, shoots starting to rise from the ground, immature flower buds, inflorescences, crown segments, leaf segments, or any part thereof. A "callus" is a mass of unorganized parenchyma cells derived from plant tissue or explants. Calli can differentiate into whole plants through the process of regeneration.

A "woody plant" is a plant with hard lignified tissues or woody parts especially stems and buds. Woody plants are typically perennial plants and include trees, shrubs, and lianas. Additional examples of woody plants include, but are not limited to fruit trees, acacia, alder, aspen, beech, birch, sweet gum, sycamore, poplar, willow, fir, pine, spruce, larch, cedar, and hemlock.

A "citrus" is a plant of the genus *Citrus* or a related genus. The *Citrus* genus includes the trees and shrubs of the rue family (Rutaceae). A "mature citrus" flowers and produces fruit.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746).

The present invention provides methods and compositions for the efficient genetic transformation of cells of commercially important plants, such as citrus plant cells, including widely used 'Hamlin' and 'Valencia' scions and 'Carrizo' rootstock by *Sinorhizobium*. The invention overcomes substantial limitations in the art, including limited transformation efficiency of mature citrus by *Agrobacterium*, and failure to describe techniques generally useful for transformation and regeneration of mature citrus plants, including 'Hamlin' and 'Valencia' varieties, by use of non-Agrobacterial strains. For example, while use of bacteria other than *Agrobacterium* has been achieved for several plant species and varieties, transformation frequencies have been low.

To date considerable research had been required in many instances to apply even well developed transformation procedures such as *Agrobacterium*-mediated transformation to different plant species. Different species within the Rhizobiales exhibit different host ranges and different abilities to attach to different plant tissues. Plants of different species often exhibit substantial physiological differences that effect amenability to genetic transformation. Methods for transformation of one species of plant therefore often do not work effectively, if at all, with other plants and the ability to transform a plant is not necessarily predictive of the ability to transform even related species using that procedure. This is particularly true for bacterial transformation of plants, which involves complex biochemical interactions between the bacterial strains used and target plant cells. Rhizobia interact with plants in the native environment and therefore can exhibit host-specificities, the impact of which is unknown for many crop species.

Thus, identifying plants amenable to Rhizobia-mediated transformation, and developing procedures allowing increased transformation efficiencies is of great interest. The present invention overcomes limitations in the art by providing, in one embodiment, techniques for the use of Rhizobiaceae, (e.g., Rhizobia or *Agrobacterium*) to transform commercially important plants, such as members of the Rutaceau (e.g., citrus). Members of the Rutaceae, including citrus, were not previously known to be transformable by Rhizobia. The invention also provides techniques for the efficient transformation of citrus plants using Rhizobia or *Agrobacterium*, including juvenile or mature citrus, which was already known to be amenable to transformation by *Agrobacterium* but at a low frequency. The invention also provides methods for the transformation of tissue targets differing from those of *Agrobacterium*. For example, while *Agrobacterium* typically requires a wound site to infect plants, some other members of the Rhizobiales, including Rhizobiaceae such as *Sinorhizobium*, naturally infect plant roots via infection threads that penetrate plant tissues, allowing for use of non-wounded tissue as a transformation target.

The goal in many cases may be to maximize transmission of an infectious DNA agent into intact, standing citrus plants.

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including fruit ripening (U.S. Pat. No. 5,512,466), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648), and improved flavor (U.S. Pat. No. 6,011,199). Any of these or other genetic elements, methods, and transgenes may be used with the invention as will be appreciated by those of skill in the art in view of the instant disclosure.

Alternatively, the nucleic acid of interest can affect these phenotypes by the inhibition of expression of an endogenous gene via gene silencing technologies such cosuppression, antisense, RNAi, expression of miRNAs (natural or engineered), expression of trans-acting siRNAs, and expression of ribozymes (see e.g., U.S. Patent Application Publication 20060200878).

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term "exogenous"

is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

While various embodiments of the present invention have been described above, it should be understood that they have been presented by way of example only, and not limitation. The present invention is not limited to the described compositions and methods, nor is it limited to a particular protein or material, nor is the present invention limited to a particular scale or batch size of production. Thus, the breadth and scope of the present invention should not be limited by any of the above-described exemplary embodiments, but should be defined only in accordance with the following claims and their equivalents.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Sinorhizobium and Agrobacterium Strains

Sinorhizobium meliloti strain 1021 carries hypervirulence plasmid pTiWB3, which is a disarmed Ti plasmid (pEHA105) derived from Agrobacterium tumefaciens strain C58 with an added broad host range origin of replication, oriT (Broothaerts et al., 2005) and was obtained from CAMBIA (Canberra, Australia). S. meliloti strains were grown in TY (Tryptone 0.5%, Yeast Extract 0.3% and 7 mM calcium chloride) medium.

Agrobacterium tumefaciens strain AGL1 is a recombination deficient (recA minus) derivative of AGL0, which carries the hypervirulent, disarmed Ti plasmid (pTiBo542) plasmid in a C58 background; and was obtained from G. Lazo (Lazo et al., 1991). Agrobacterium strains were grown in YEP (Yeast Extract 1%, Peptone 1% and 0.5% sodium chloride) medium.

Example 2

Transformation of Sinorhizobium and Agrobacterium

Sinorhizobium competent cells were prepared by washing a log phase culture in TY medium with chilled deionized water and 10% glycerol, and stored at −80° C. Binary vector pIPG955 (FIG. 1) was introduced by electroporation using 100 µl of thawed S. meliloti 1021/pTWBi3 competent cells mixed with 0.5 µg of pIPG955 and incubated on ice for 30 min. The mixture was transferred into a pre-chilled cuvette (1 mm gap) and electroporated at 1100 volts using an Eppendorf 2510 electroporator (Hauppauge, N.Y.). The mixture was transferred into 1 ml of TY medium and incubated at 28° C. with shaking at 150 rpm for 16 hr. 200 µl of the medium was spread on a TY agar plate containing 100 µg/ml spectinomycin (to select pIPG955) 250 µg/ml of streptomycin (to select for strain 1021) and 150 µg/ml of kanamycin (to select for pTWBi3). The plate was incubated at 28° C. for 3 days.

Figure 2:
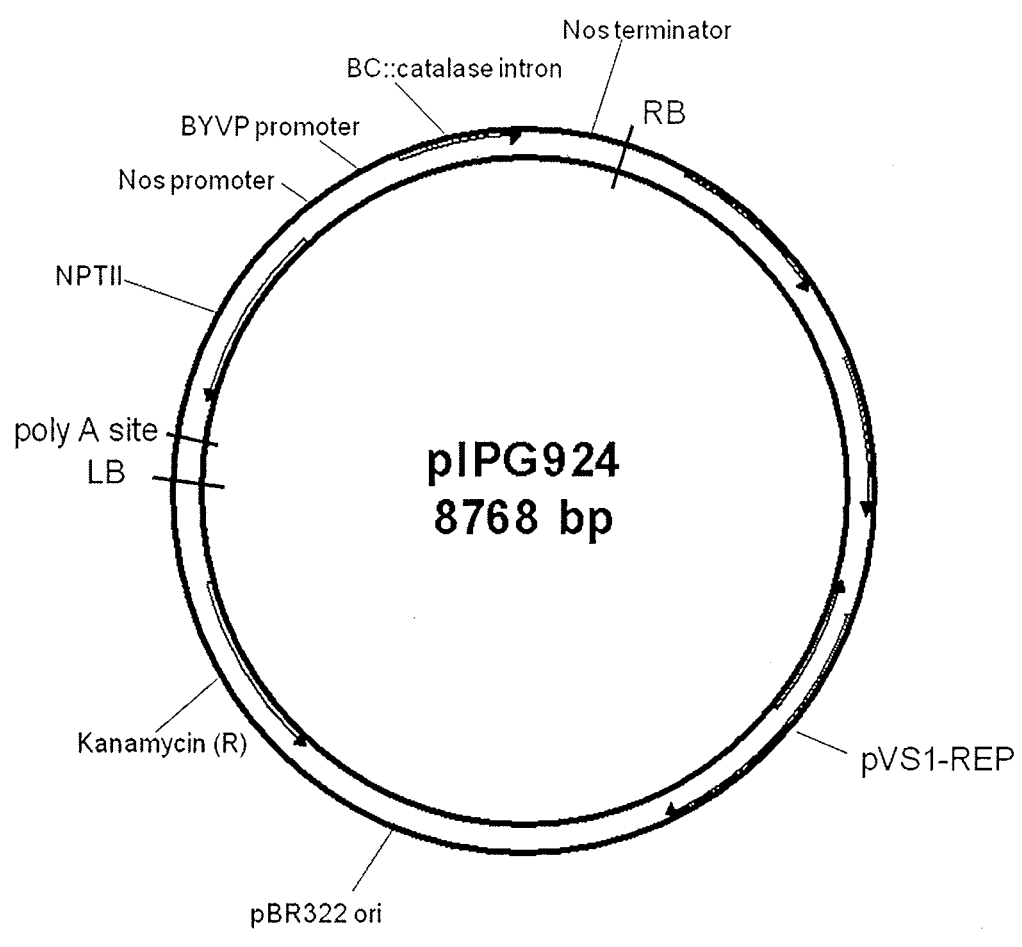
FIG. 2: Schematic map of pIPG924. LB, Left T-DNA border; RB, Right T-DNA border.

Agrobacterium competent cells were prepared by washing a log phase culture in YEP medium with chilled deionized water and 10% glycerol, and stored at −80° C. Binary vector pIPG924 (FIG. 2) was introduced by electroporation using 100 µl of thawed A. tumefaciens AGL1/pTiBo542 competent cells mixed with 0.5 µg of pIPG924 and incubated on ice for 30 min. The mixture was transferred into a pre-chilled cuvette (1 mm gap) and electroporated at 1100 volts using an Eppendorf 2510 electroporator (Hauppauge, N.Y.). The mixture was transferred into 1 ml of YEP medium and incubated at 28° C. with shaking at 150 rpm for 2 hr. 20 µl of the medium was spread on a YEP agar plate containing 40 µg/ml kanamycin to select pIPG924. The plate was incubated at 28° C. for 2 days.

Example 3

Binary Transformation Vectors

Figure 7:
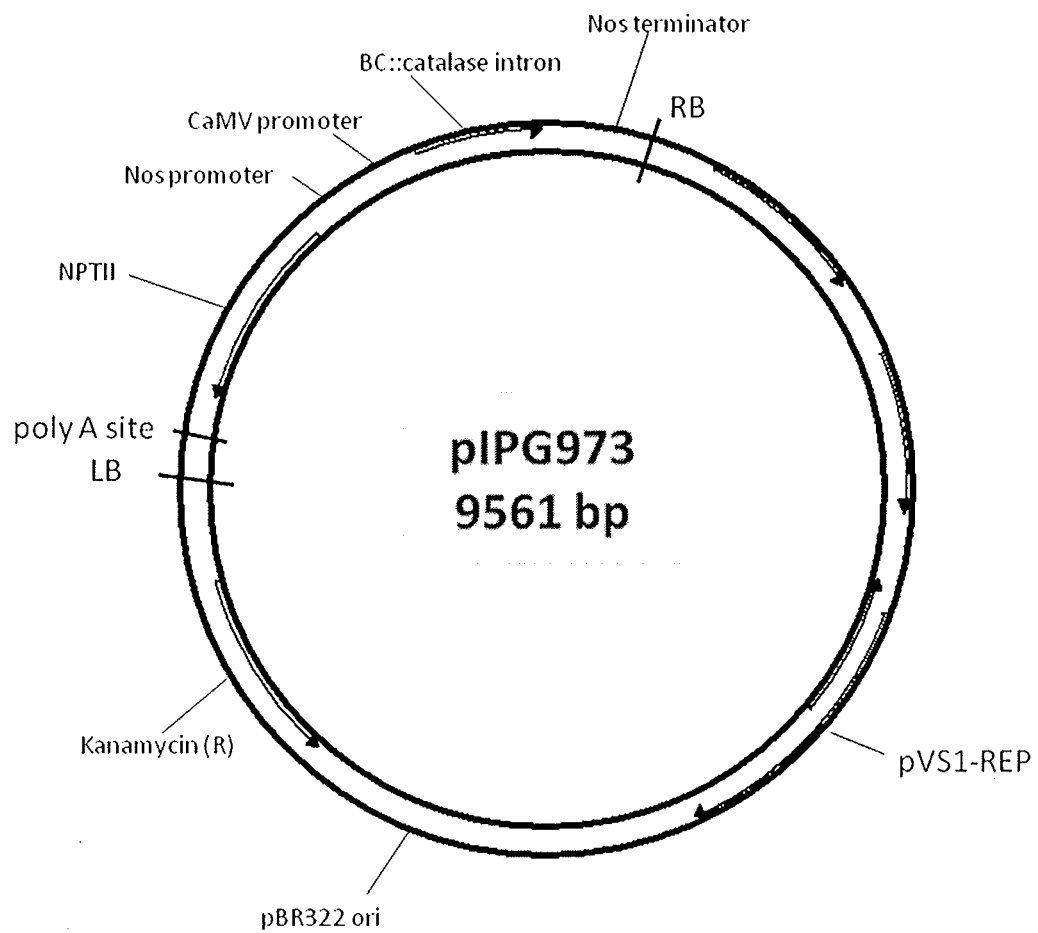
FIG. 7: Schematic map of pIPG973. LB, Left T-DNA border; RB, Right T-DNA border.
Figure 8:
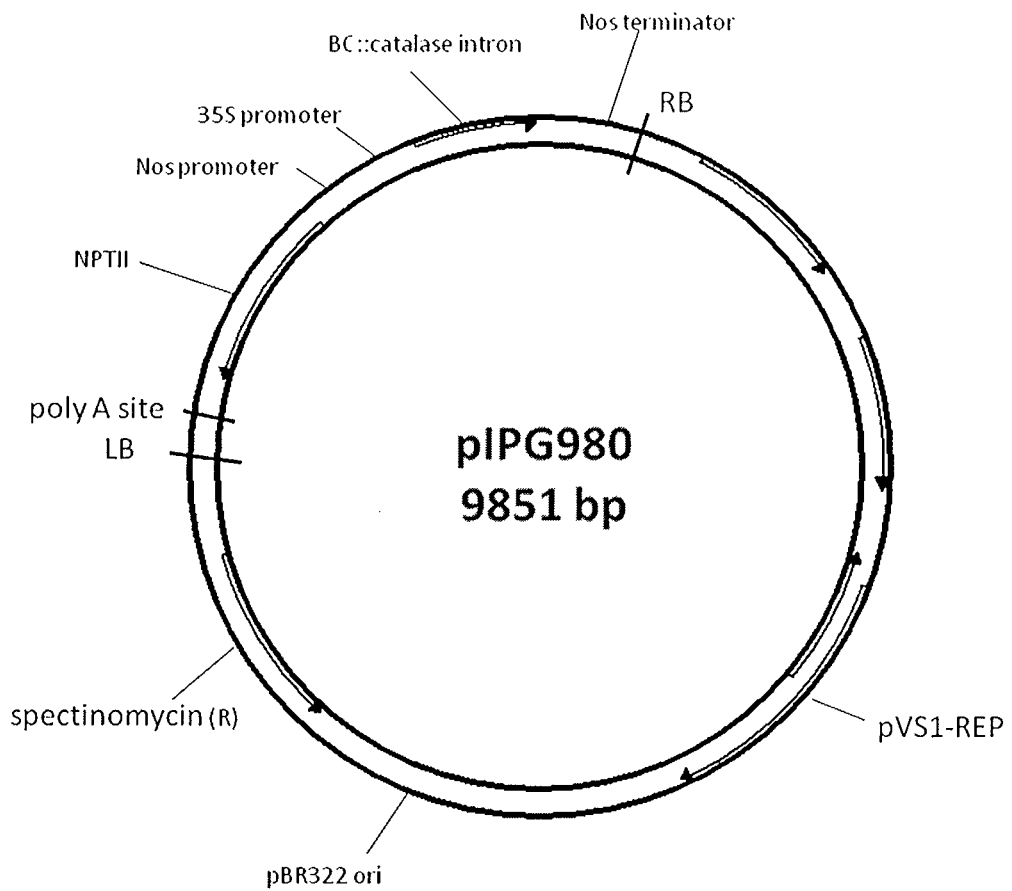
FIG. 8: Schematic map of pIPG980. LB, Left T-DNA border; RB, Right T-DNA border.

Binary transformation vectors were constructed using standard molecular techniques known to those skilled in the art. Plasmid constructs pIPG955 (FIG. 1; SEQ ID NO: 1) and pIPG980 (FIG. 8; SEQ ID NO: 4) were made for use in non-Agrobacterium strains. Plasmid constructs pIPG924 (FIG. 2; SEQ ID NO: 2) and pIPG973 (FIG. 7; SEQ ID NO: 3) were made for use in Agrobacterium strains. All constructs were based on pCAMBIA2301 (Cambia, Canberra, Australia), and all carry both a pVS1 wide host range replication origin and a pBR322 replication origin for high copy maintenance in E. coli. pIPG924 was constructed by first replacing the double 35S promoter of pCAMBIA2301 with the nopaline synthase (nos) promoter which was used to drive the neomycin phosphotransferase gene (nptII) gene, which confers resistance to kanamycin, for selection in citrus. The 35S::GUS gene was then replaced with the virus coat protein controller element from Beet Yellows Closterovirus (BYV), from nucleotides 13499-13637 (Peremyslov et al., 1999), operationally fused to the anti-bacterial BC gene interrupted with the catalase intron (see U.S. Pat. No. 7,919,601 and PCT/US08/70612, which are incorporated by reference herein). pIPG973 was identical to pIPG924, except that the single 35S promoter was used to replace the BYVP promoter found in pIPG924.

pIPG955 was constructed similarly to pIPG924, with the double 35S promoter of pCAMBIA2301 replaced with the nos promoter to drive the nptII gene, which confers for selection in citrus, followed by replacing the GUS gene with a BC::intron fragment and with a glycine rich peptide (GRP) leader, operationally driven by the single 35S promoter. In addition, the bacterial kanamycin resistance gene was replaced with a spectinomycin resistance gene fragment from pCAMBIA1105 for use in non-Agrobacteria strains carrying pTWBi3. pIPG980 was identical to pIPG955, except that the GRP leader was deleted, and the intron was moved further downstream in the BC gene.

pIPG955 was transferred into *S. meliloti*/pTWBi3 by electroporation and confirmed by PCR analysis of miniprep DNA. pIPG924 was transferred into *A. tumefaciens* AGL1/pTiBo542 by electroporation and confirmed by similar PCR analysis.

Example 4

Extraction of Binary and Disarmed Ti Helper Plasmids from *Sinorhizobium*

The disarmed Ti helper plasmids, pTWBi3 and pTiBo542, together with binary plasmids pIPG955 and pIPG924 were extracted from *S. meliloti* 1021, and *A. tumefaciens* AGL1, respectively. Briefly, five mls of overnight culture in TY with kanamycin 150 mg/l, streptomycin 250 mg/l and spectinomycin 100 mg/l was spun down, resuspended in 250 µl of P1 buffer, mixed with 250 µl of P2 buffer, and neutralized with 350 µl P3 buffer (buffers from QIAGEN maxi-prep kit). After 5 min incubation at room temperature, the mixture was spun for 10 min at 12,000 g at 4° C. Approximately 750 µl of supernatant was mixed with 750 µl of isopropanol and spun for 10 min at 4° C. The pellet was washed with 70% ethanol once and resuspended in 50 µl of TE without drying. The plasmid preps were subsequently stored at 4° C. The plasmid DNA was used as a template for PCR analysis using the methods described by Broothaerts (2005). The pIPG955 and pIPG924 plasmids were retransformed back into *E. coli*, then the plasmids were re-extracted in higher copy and the insert sequenced to determine stability after passage through *S. meliloti* or *A. tumefaciens*.

Example 5

*Sinorhizobium meliloti*-Mediated Juvenile Citrus Transformation

Citrus cultivar 'Carrizo' was obtained as seeds from a State of Florida certified seed producer and surface sterilized 'Carrizo' seeds were used for *S. meliloti*-mediated transformation. To surface sterilize the seeds, the outer seed coat was removed by manual peeling, and the peeled seeds were then placed in 70% isopropanol for 2-3 minutes. The isopropanol was poured off and 100 ml of 0.6% sodium hypochlorite solution was added for 10 min. The chlorine solution was poured off and the seeds were rinsed 3× with sterile deionized water. The seeds were blotted on paper towels and 1-2 seeds were placed onto ca. 6 ml of solidified Germination medium in 8" (large) sterile test tubes. Germination medium consists of 0.5×MS salts, 1.5% sucrose, and 0.7% agar, pH 5.7. Seeds were then allowed to germinate and grow in a dark incubator at 26° C. Etiolated citrus seedlings from 4-5 week old cultures were used as the explant source.

Explants were prepared under sterile conditions by cutting approximate 1 cm long epicotyl sections from the etiolated seedlings. Epicotyl sections were covered with Presoak medium (consisting of 0.5×MS salts, 8% maltose, 0.05% MES, full strength MS vitamins, pH5.7) for 30 minutes at room temperature.

Following the presoak, the medium was poured off and replaced by covering the explants for 20 minutes with a suspension of *S. meliloti* bacteria prepared as follows: a 20 ml overnight starter culture of *S. meliloti*/pTWBi3 containing pIPG955 was grown from a single colony in TY medium with kanamycin 150 mg/l, and spectinomycin 100 mg/l. The cells were collected by centrifugation at 3000×g for 10 minutes, and rinsed 2-3× with Tomato Transformation (TMT) medium (1×MS salts, 3% sucrose, pH 5.8) plus 100 µM acetosyringone. Cells were resuspended in ca. 50 ml TMT+100 µM acetosyringone, the cell density adjusted to O.D.=1.0, and gently shaken for 30-60 minutes.

The *S. meliloti* suspension was poured off, and the inoculated explants were blotted dry and placed onto Co-cultivation plates, and incubated for about 9-12 days at 25° C. in continuous dark. Explants exhibiting *S. meliloti* overgrowth were placed on fresh Co-cultivation plates during this time. Co-cultivation medium consisted of: 1×MS salts, 3% sucrose, full strength MS Vitamins, 1 mg/l BAP, 0.5 mg/l NAA, 0.7% agar, pH 5.7.

After dark incubation, explants were transferred to Regeneration medium with kanamycin selection (1×MS salts, 3% sucrose, full strength MS Vitamins, 1 mg/l BAP, 0.5 mg/l NAA, 250 mg/l cefotaxime, 25 mg/l kanamycin sulfate, 0.7% agar, pH 5.7) and maintained in the dark for an additional 3-6 days at 26° C., to total 15 days in the dark. Plates were then transferred to a growth chamber for 15-30 days at 26° C. with a 16/8 hour light-dark photo period until shoots emerged. Explants with shoots were then transferred onto the surface of the Shoot Elongation medium (1×MS salts, 3% sucrose, full strength MS Vitamins, 0.5 mg/l BAP, 0.1 mg/l NAA, 250 mg/l cefotaxime, 25 mg/l kanamycin sulfate, 0.7% agar, pH 5.7). Shoot elongating to a length greater than 1 cm were removed from the explant and transferred to Rooting Medium 1, [0.25× MS salts, 2% sucrose, ¼ strength MS Vitamins, 5 mg/l IBA (indole-butyric acid), 0.5 mg/l NAA, 250 mg/l cefotaxime, 0.7% agar, pH 5.7] for 7-10 days at 26° C. with a 16/8 hour light-dark photo period.

Shoots were then transferred to Rooting Medium 2 plates (0.25×MS salts, 2% sucrose, ¼ strength MS Vitamins, 250 mg/l cefotaxime, 0.7% agar, pH 5.7) for 7-20 days at 26° C. with a 16/8 hour light-dark photo period. Rooted shoots were then transferred again to Rooting Medium 2 in standard test tubes (about 3" of medium in the tube) to allow root growth. After roots were ca 2" long, plants were transferred to soil and the pot was covered with plastic to keep humidity high for a period of about 1 week. Plastic was then removed after vigorous growth was observed. Plants were held for an additional 3 weeks until multiple leaves were produced. One leaf was removed for protein extraction and testing for expression of the transgene by Western blot. The rooted plantlets were transferred to the greenhouse for further growth and testing.

Figure 3:
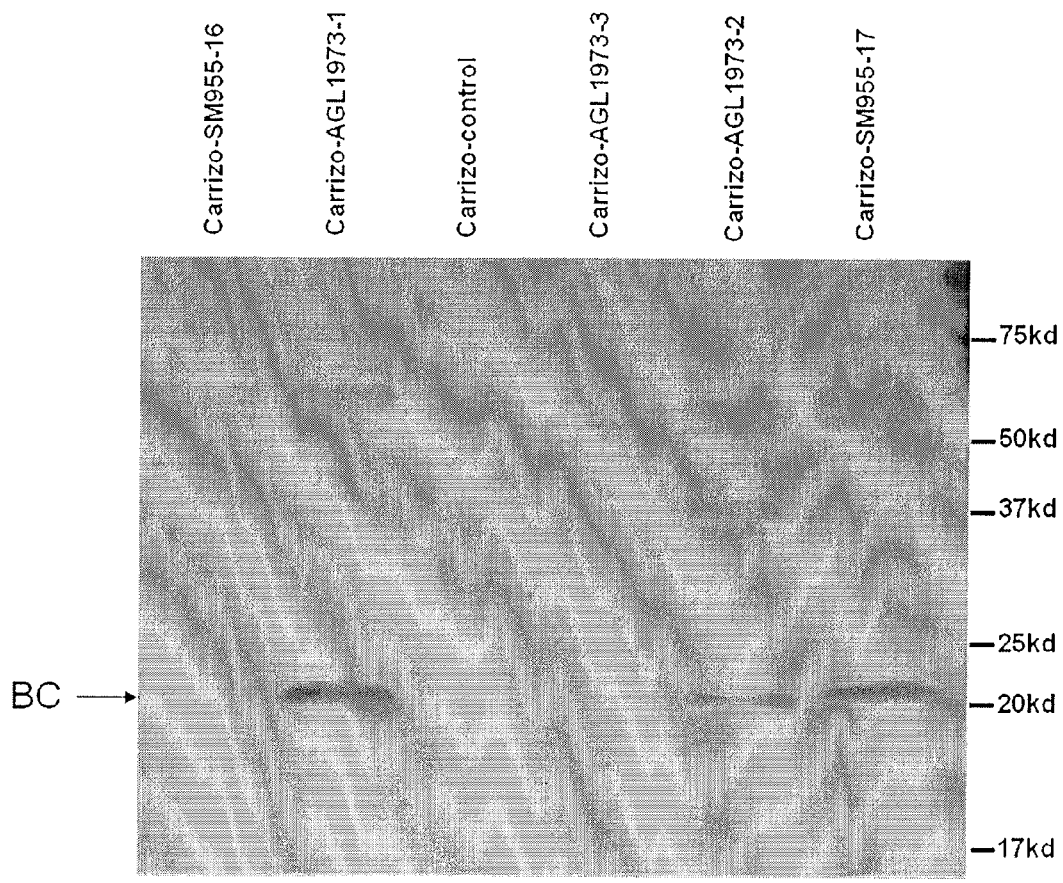
FIG. 3: Western blot of transgenic, self-rooted 'Carrizo' created by use of *S. meliloti* (SM955-16 and SM955-17) and *A. tumefaciens*, (AGL1973-1, -2 and -3) showing expression of BC using anti-BC protein antibody.

Based on Western blot analyses, *S. meliloti* delivered T-DNA carrying the desired transgene BC into juvenile citrus cv. 'Carrizo' cells, resulting in completely transgenic, rooted 'Carrizo' citrus plants expressing the desired transgene (FIG. 3 and Table 1). Transgenic rooted juvenile citrus plants were obtained from *S. meliloti*-mediated transformation experiments by a direct transformation method at frequencies ranging from 1.5 to 4.7% of the starting number of explants. The transgenic nature of these citrus plants was confirmed by Western blot.

TABLE 1

*S. meliloti*-mediated juvenile citrus transformation summary.

| Experiment batch # | 12/30 | 12/20 | 01/03 |
|---|---|---|---|
| starting # explants | 206 | 116 | 193 |
| # shoots on kanamycin | 26 (13%) | 15 (13%) | 41 (21%) |
| # rooted shoots | 3 (1.5%) | 2 (1.7%) | 9 (4.7%) |

Example 6

*Sinorhizobium meliloti*-Mediated Juvenile Citrus Transformation Using Preconditioned Explants without Meristematic Tissue Citrus cultivar 'Carrizo' was obtained as seeds from a State of Florida certified seed producer, surface sterilized and germinated in the dark as described in Example 5. Etiolated citrus seedlings from 4-5 week old cultures were used as the explant source.

Explants were prepared under sterile conditions by cutting approximate 1 cm long epicotyl sections from the etiolated seedlings. Epicotyl sections were covered with Presoak medium (consisting of 0.5×MS salts, 8% maltose, 0.05% MES, pH5.7) for 30 minutes at room temperature.

Following Presoak, the medium was poured off and explants were blotted dry and transferred to Regeneration medium without selection (1×MS salts, 3% sucrose, full strength MS Vitamins, 1 mg/l BAP, 0.5 mg/l NAA, 250 mg/l cefotaxime, 0.7% agar, pH 5.7) and maintained in the dark at 26° C., until callus was observed on the cut surfaces of the explants (about 15 days). Explants exhibiting callus formation were selected, and any callus and meristamtic tissue that had formed was completely removed using a scalpel immersed prior to cutting in *S. meliloti* inoculum, prepared as exactly described in Example 5. Explants were then blotted dry and transferred to Co-cultivation plates, and incubated for about 9-12 days at 25° C. in continuous dark. Explants exhibiting *S. meliloti* overgrowth were placed on fresh Co-cultivation plates during this time. Co-cultivation medium consisted of: 1×MS salts, 3% sucrose, full strength MS Vitamins, 1 mg/l BAP, 0.5 mg/l NAA, 0.7% agar, pH 5.7.

All subsequent regeneration steps, including shoot emergence and rooting, were performed exactly as described in Example 5.

Based on Western blot analyses, *S. meliloti* delivered T-DNA carrying the desired transgene BC into juvenile citrus cv. 'Carrizo' cells using this preconditioning method, resulting in completely transgenic, rooted 'Carrizo' citrus plants expressing the desired transgene (FIG. 3 and Table 1). Transgenic rooted juvenile citrus plants were obtained from *S. meliloti*-mediated transformation experiments by a preconditioning method at frequencies ranging from 2 to 5% of the starting number of explants. The transgenic nature of these citrus plants was confirmed by Western blot.

TABLE 2

| *S. meliloti*-mediated juvenile citrus transformation summary (preconditioning method). | | |
|---|---|---|
| Experiment batch # | 03/23 | 04/29 |
| starting # explants | 80 | 500 |
| # shoots on kanamycin | 24 (30%) | 49 (10%) |
| # rooted shoots | 4 (5%) | 10 (2%) |

Example 7

Comparative *Agrobacterium tumefaciens*-Mediated Juvenile Citrus Transformation In order to compare the transformation frequencies obtained using *S. meliloti* with the same method on the same tissue, but instead using *Agrobacterium*, *A. tumefaciens* AGL1 was used for transformation. Citrus cultivar 'Carrizo' was obtained as seeds from a State of Florida certified seed producer, surface sterilized and germinated in the dark as described in Example 5. Etiolated citrus seedlings from 4-5 week old cultures were used as the explant source. Citrus tissue was prepared and treated exactly as described in Example 5, except that the explants were incubated for 10 minutes with a suspension of *A. tumefaciens* bacteria prepared as follows: a 20 ml overnight starter culture of *A. tumefaciens* AGL1 containing pIPG924 was grown from a single colony in YEP medium with kanamycin 40 mg/l. The cells were collected by centrifugation at 3000×g for 10 minutes, and rinsed 2-3× with TMT medium (1×MS salts, 3% sucrose, pH 5.8) plus 100 uM acetosyringone. Cells were resuspended in ca. 50 ml TMT+100 uM acetosyringone, the cell density adjusted to O.D.=0.3, and gently shaken for 30-60 minutes.

The *A. tumefaciens* suspension was poured off, and the inoculated explants were blotted dry and placed onto Co-cultivation plates, and incubated for about 2 days at 25° C. in continuous dark as described in Example 5. After 2 days of co-cultivation, explants were transferred to Regeneration medium with kanamycin as described in Example 5 for 15 days in continuous dark. Thereafter, explants were transferred to a growth chamber for 15-30 days at 26° C. with a 16/8 hour light-dark photo period until shoots emerged and otherwise further treated as described in Example 5.

Based on Western blot analyses, *Agrobacterium* delivered T-DNA carrying the desired transgene BC into juvenile citrus cv. 'Carrizo' cells, resulting in completely transgenic, rooted 'Carrizo' citrus plants expressing the desired transgene (FIG. 3 and Table 3). Transgenic rooted juvenile citrus plants were obtained from *Agrobacterium*-mediated transformation experiments at frequencies ranging from 2.7% to 3.6% of the starting number of explants, which is comparable to the 1.5 to 4.7% obtained using *Sinorhizobium*. Interestingly the number of kanamycin resistant shoots was 17%. The transgenic nature of these citrus plants was confirmed by Western blot.

TABLE 3

| *Agrobacterium*-mediated juvenile citrus transformation summary. | | |
|---|---|---|
| Experiment batch # | 11/10 | 11/15 |
| starting # explants | 186 | 112 |
| # shoots on kanamycin | 32 (17%) | 19 (17%) |
| # rooted shoots | 5 (2.7%) | 4 (3.6%) |

Example 8

*Sinorhizobium meliloti*-Mediated Mature Citrus Transformation Using Preconditioned Explants without Meristematic Tissue As starting material, shoots of mature citrus cultivars 'Hamlin', 'Valencia' and 'Mid-Sweet' sweet orange trees which were grafted or "budded" onto juvenile citrus cultivars 'Carrizo' or 'Swingle' rootstock from a commercial citrus nursery were used. Young, freshly emerged, semi-hard shoots of about 6-8" in length, representing the first 2 or 3 flushes after the graft from the freshly budded nursery trees were removed and placed immediately in water. Alternatively, fully emerged, hardened, triangular main stems of young grafted trees, about 12-18" in length, may be used, avoiding the woody, round portion of the stems. Leaves and thorns were removed and rinsed twice in distilled water. This tissue was surface sterilized by immersion for 8-10 min (30 minutes for triangular main stems) in 1.2% chlorine bleach (2.4% for triangular main stems) with a few drops of Tween-20 added. The tissue was then rinsed 5×, each time by immersion for 2 minutes using sterile deionized water. The ends were cut away and discarded, and approximate 1 cm long internodal sections were cut and retained. These explants were covered with Presoak medium (consisting of 0.5×MS salts, 8% maltose, 0.05% MES, pH5.7) for 10 minutes at room temperature.

Following the presoak, the medium was poured off and explants were blotted dry and transferred to Shoot Induction Medium (1×MS salts, 2.5% sucrose, full strength MS Vitamins, 3 mM MES, 250 mg/l PVP-40, 20 ml/l coconut milk, 1 mg/l BAP, 0.5 mg/l NAA, 250 mg/l cefotaxime, 100 mg/l carbenicillin, 10 mg/l silver nitrate, 0.7% agar, pH 5.7) for 2-4 weeks in the dark at 26° C., until callus was observed on the cut surfaces of the explants (about 2-4 weeks). Explants exhibiting callus formation were selected, and any callus and meristematic tissue that had formed was completely removed using a scalpel. In some experiments, the scalpel was immersed prior to cutting in S. meliloti inoculum. In some experiments, the cut pieces were immersed in the S. meliloti inoculum.

S. meliloti inoculum was prepared as follows: a 20 ml overnight starter culture of S. meliloti/pTWBi3 containing pIPG955 was grown from a single colony in TY medium with kanamycin 150 mg/l, and spectinomycin 100 mg/l. Fifty µl of this culture was inoculated to 150 ml of TY medium and grown overnight to an OD=1.0. The cells were collected by centrifugation at 3000×g for 10 minutes, and rinsed with Mature Citrus Transformation (MCT) medium (1×MS salts, 8% sucrose, 3 mM MES, 250 mg/l PVP-40, 20 ml/l coconut milk, pH 5.7). Cells were resuspended in 150 ml MCT, and gently shaken for 30-60 minutes. Acetosyringone (200 µM) was added immediately prior to contacting plant tissue with these cells.

Following S. meliloti inoculation, explants were blotted dry and transferred to Co-cultivation medium (CCM) plates, and incubated for 9-12 days at 25° C. in continuous dark. Co-cultivation medium consisted of: 1×MS salts, 2.5% sucrose, full strength MC Vitamins, 3 mM MES, 250 mg/l PVP-40, 20 ml/l coconut milk, 1 mg/l BAP, 0.5 mg/l NAA, 10 mg/l silver nitrate, and 0.7% agar, pH 5.7. Explants exhibiting S. meliloti overgrowth were placed on fresh CCM plates during this time.

After 9-12 days on CCM medium in the dark, explants were transferred to Shoot Induction Medium (SIM), which consists of CCM plus 200 mg/l cefotaxime, and 100 mg/l carbenicillin and maintained in the dark for an additional 1-4 weeks at 26° C., for a total of 2-8 weeks incubation in the dark to encourage callus formation. Explants exhibiting callus formation were then transferred to fresh SIM plates containing 20 mg/l kanamycin sulfate. Plates were then transferred to a growth chamber for 2-8 weeks at 26° C. with a 16/8 hour light-dark photo period until shoots emerged.

Explants with shoots were then transferred onto the surface of Shoot Elongation medium (SEM), comprised of 1×MS salts, 2.5% sucrose, full strength MS Vitamins, 3 mM MES, 0.5 mg/l BAP, 0.1 mg/l NAA, 250 mg/l cefotaxime, 100 mg/l carbenicillin, 20 mg/l kanamycin sulfate, 0.7% agar, pH 5.7. Shoots elongating to a length greater than about 1 cm were removed from the explant and grafted onto non-transgenic or transgenic 'Carrizo' rootstocks grown in soil from seeds.

Figure 4:
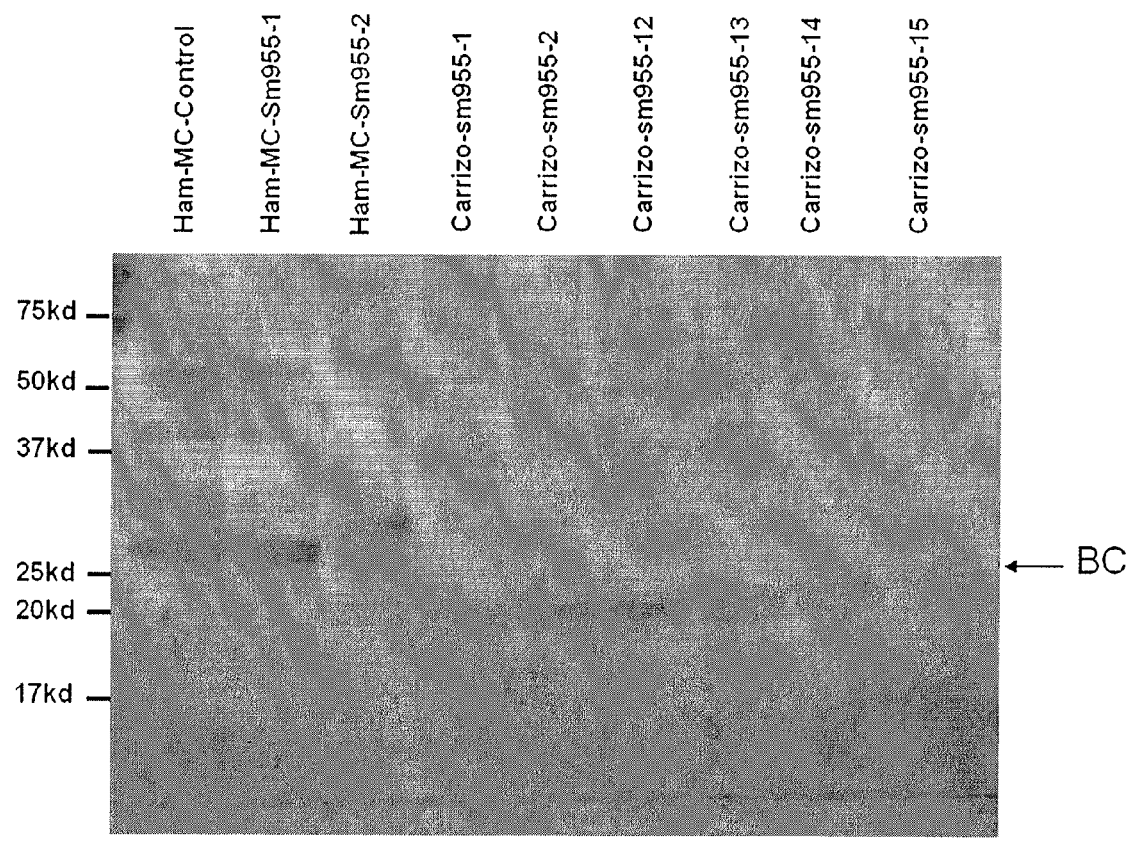
FIG. 4: Western blot of transgenic mature 'Hamlin' scion (MC-Sm955-2) and transgenic self-rooted 'Carrizo' (sm955-1. -2, -12, -13, -14 and -15) created by use of *S. meliloti*, showing expression of BC using anti-BC protein antibody.
Figure 6:
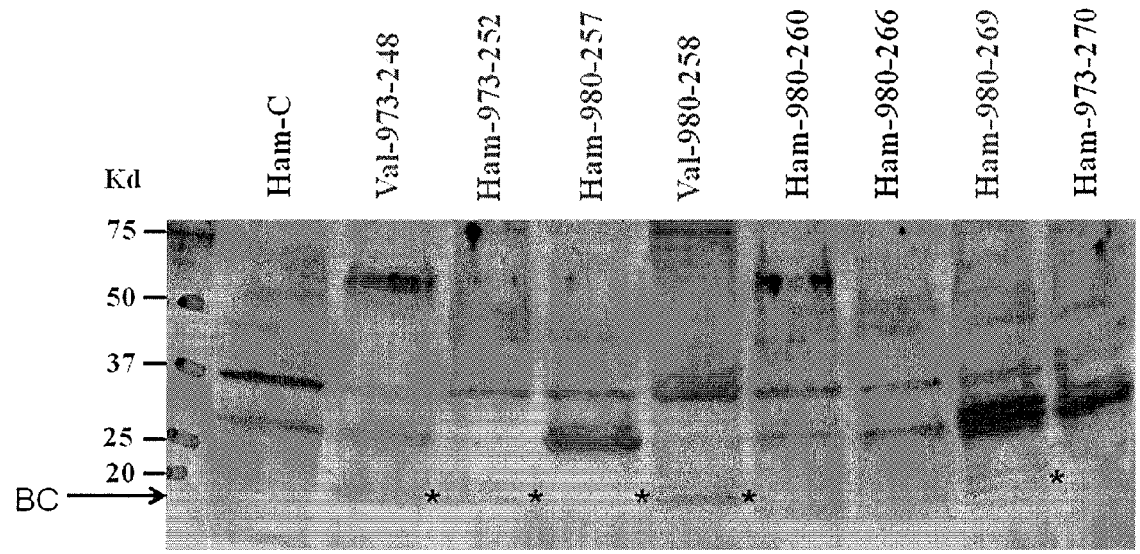
FIG. 6: Western blot of transgenic, mature 'Hamlin' (Ham-980-257 and -269) and 'Valencia' (Val-980-258) created by use of *S. meliloti* and transgenic mature 'Hamlin' (Ham-973-252) and 'Valencia' (Val-973-248) created by use of *Agrobacterium*, showing expression of BC using anti-BC protein antibody. A nontransgenic 'Hamlin' control (Ham-C) and several nonexpressing 'Hamlin' escapes (Ham-973-270, 980-260, and -266) are also shown.

Based on Western blot analyses, S. meliloti delivered T-DNA carrying the desired transgene BC into mature citrus cv. 'Hamlin' and 'Valencia' cells using this preconditioning method, resulting in completely transgenic scions expressing the desired transgene (FIGS. 4 & 6 and Table 4), grafted onto 'Carrizo' citrus plants. Transgenic mature citrus plants were obtained from S. meliloti-mediated transformation experiments by a using this preconditioning method at a frequency of about half of the number of successfully grafted shoots. Successfully grafted shoots were obtained at frequencies ranging from 0.8%-12% of the starting number of explants. The transgenic nature of roughly half of these citrus scion plants (0.4% to 6%) was confirmed by Western blots (FIGS. 4 & 6; some data not shown).

TABLE 4

S. meliloti-mediated mature citrus transformation summary.

| Experiment batch # | 03/16 | 9/14 | 3/7 | 4/18 |
|---|---|---|---|---|
| starting # explants | 161 | 118 | 130 | 649 |
| # explants with shoots on kanamycin | 3 (2%) | 1 (0.8%) | 15 (11.5%) | 82 (12.6%) |
| # grafted shoots | 1 (0.6%) | 1 (0.8%) | 16 (12%) | 14 (2%) |

Example 9

Grafting of Mature Transformed Shoots onto Rootstocks Grown in Soil from Seeds

One to two month old citrus cultivar 'Carrizo' seedlings grown in soil (of about 6-10" in height) were obtained from a State of Florida certified nursery. All leaves were removed from each seedling, and the entire stem was gently surface sterilized using a paper towel soaked in 70% ethanol. The apical tip of the stem was removed using a sterile scalpel above the top node, leaving about 1 cm of internode. The scalpel is then used to create a longitudinal cut about 5 mm deep from the top of the cut stem, and splitting the stem into a V-shape. A drop of sterile water was then added into the V-cut to keep the area moist while the scion was prepared for grafting.

Transformed mature citrus explants with shoots elongated to a length greater than about 1 cm (usually with 2-3 leaves) were removed from tissue culture, and the elongating shoot was cut away from the explant, creating a V-shaped cut in the lower part of the stem. The V-Shaped cut in the mature scion was then carefully placed into the V-shaped cut in the rootstock, and the surfaces carefully formed together and were held in place by use of 2.0 mm grafting clips. A plastic polyethylene fold-top sandwich bag was then carefully placed over the entire grafted scion without touching the grafted union and slowly squeezed shut, fully enclosing the grafted scion above the soil line. The enclosure was kept in place by use of a clip placed below the graft union and above the soil line. The sides of the inflated bag were held in place by two short wooden sticks (barbecue skewers), placed in the pot and attached to the plastic bag enclosure by tape. Approximately 10 ml of sterile water was then injected into the plastic bag enclosure using a tuberculin syringe.

Grafted plants were then incubated at 27 C, in a growth chamber equipped with fluorescent light (16 hr. photoperiod) for two weeks. Water inside of the enclosure was replaced as necessary using a tuberculin syringe. Grafted plants were then transferred to a higher light intensity growth room and kept for two additional weeks.

Example 10

Sinorhizobium meliloti-Mediated Mature Citrus Transformation Using Preconditioned Explants with Meristematic Tissue As starting material, shoots of mature citrus cultivars 'Hamlin', 'Valencia' and 'Mid-Sweet' sweet orange trees which were grafted or "budded" onto juvenile citrus cultivars 'Carrizo' or 'Swingle' rootstock from a commercial citrus nursery were used. Young, freshly emerged, semi-hard shoots of about 6-8" in length, representing the first 2 or 3 flushes after the graft from the freshly budded nursery trees were removed and placed immediately in water. Leaves and thorns were removed and rinsed twice in distilled water. This tissue was surface sterilized by immersion for 8-10 min in 1.2% chlorine bleach with a few drops of Tween-20 added. The tissue was then rinsed 5×, each time by immersion for 2 minutes using sterile deionized water. The ends were cut away and discarded, and approximate 1 cm long internodal sections were cut and retained. All nodes were discarded. These explants were covered with Presoak medium (consisting of 0.5×MS salts, 8% maltose, 0.05% MES, pH5.7) for 10 minutes at room temperature.

Following the presoak, the medium was poured off and explants were blotted dry and transferred to Shoot Induction Medium (1×MS salts, 2.5% sucrose, full strength MS Vitamins, 3 mM MES, 250 mg/l PVP-40, 20 ml/l coconut milk, 1 mg/l BAP, 0.5 mg/l NAA, 250 mg/l cefotaxime, 100 mg/l carbenicillin, 10 mg/l silver nitrate, 0.7% agar, pH 5.7) for 2-5 weeks in the dark at 26 degrees C., until callus was observed on the cut surfaces of the explants. Explants exhibiting callus formation were selected, and transferred to the light for 1-2 weeks. Explants exhibiting primordial shoots of 1-4 mm were wounded using a tuberculin needle, punching a hole near the base of each primordial shoot. The tuberculin needle is pre-immersed (prior to wounding) in S. meliloti inoculum.

S. meliloti inoculum was prepared as follows: a 20 ml overnight starter culture of S. meliloti/pTWBi3 containing pIPG955 was grown from a single colony in TY medium with kanamycin 150 mg/l, and spectinomycin 100 mg/l. Fifty ul of this culture is inoculated to 150 ml of TY medium without antibiotic and grown overnight to an OD=1.0. The cells were collected by centrifugation at 3000×g for 10 minutes, and rinsed with Mature Citrus Transformation (MCT) medium (1×MS salts, 8% sucrose, 3 mM MES, 250 mg/l PVP-40, 20 ml/l coconut milk, pH 5.8). Cells were resuspended in 150 ml MCT, and gently shaken for 30-60 minutes. Acetosyringone was added to 200 uM and Silwet L-77 was added to 0.02% immediately prior to contacting plant tissue with these cells.

Following S. meliloti inoculation, explants are blotted dry and transferred to Co-cultivation medium (CCM) plates, and incubated for 9 days at 25.degrees C. in continuous dark. Co-cultivation medium consisted of: 1×MS salts, 2.5% sucrose, full strength MC Vitamins, 3 mM MES, 250 mg/l PVP-40, 20 ml/l coconut milk, 1 mg/l BAP, 0.5 mg/l NAA, 10 mg/l silver nitrate, and 0.7% agar, pH 5.7. Explants exhibiting S. meliloti overgrowth are placed on fresh CCM plates during this time.

After 10 days on CCM medium in the dark, explants are transferred to Shoot Induction Medium (SIM), which consists of CCM plus 200 mg/l cefotaxime, and 100 mg/l carbenicillin and maintained in the dark for an additional 1-4 weeks at 26 degrees C., to total 2-8 weeks in the dark to encourage callus formation. Explants exhibiting callus formation are then transferred to fresh SIM plates containing 20 mg/l kanamycin sulfate. Plates are then transferred to a growth chamber for 2-8 weeks at 26 degrees C. with a 16/8 hour light-dark photo period until shoots emerged.

Explants with shoots are then transferred onto the surface of Shoot Elongation medium (SEM), comprised of 1×MS salts, 3% sucrose, full strength MS Vitamins, 0.5 mg/l BAP, 0.1 mg/l NAA, 250 mg/l cefotaxime, 20 mg/l kanamycin sulfate, 0.7% agar, pH 5.7. Shoots elongating to a length greater than 1 cm are removed from the explant and grafted onto non-transgenic 'Carrizo' rootstocks grown in soil from seeds.

Example 11

Agrobacterium-Mediated Mature Citrus Transformation Using Preconditioned Explants without Meristematic Tissue As starting material, shoots of mature citrus cultivars 'Hamlin', 'Valencia' and 'Mid-Sweet' sweet orange trees which were grafted or "budded" onto juvenile citrus cultivars 'Carrizo' or 'Swingle' rootstock from a commercial citrus nursery were used and treated exactly as described in Example 8, except that A. tumefaciens AGL1 was used for transformation and the tissue was kept on CCM plates for 2 days instead of 9-12 days.

A. tumefaciens inoculum was prepared as follows: a 20 ml overnight starter culture of A. tumefaciens AGL1 containing pIPG924 was grown from a single colony in YEP medium with 40 mg/l kanamycin. Ten μl of this culture was inoculated to 50 ml of YEP medium and grown overnight to an OD of less than 0.6. The cells were collected by centrifugation at 3000×g for 10 minutes and the cell density adjusted to O.D.=0.3. The cells were re-centrifuged and rinsed with Mature Citrus Transformation (MCT) medium (1×MS salts, 8% sucrose, 3 mM MES, 250 mg/l PVP-40, 20 ml/l coconut milk, pH 5.8). Cells were resuspended in 150 ml MCT, and gently shaken for 30-60 minutes. Acetosyringone (200 uM) and Silwet L-77 was added to 0.02% immediately prior to contacting plant tissue with these cells.

Figure 5:
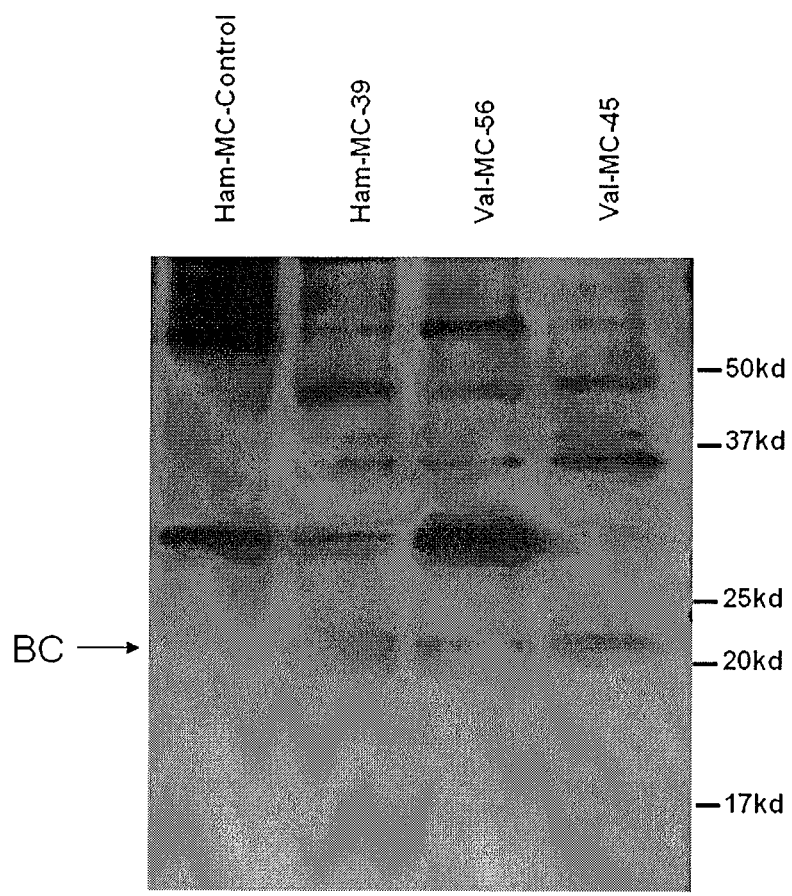
FIG. 5: Western blot of transgenic, mature 'Hamlin' (MC-39) and mature 'Valencia' (MC45, MC-56) scions created by use of *Agrobacterium*, using anti-BC protein antibody.

Based on Western blot analyses, A. tumefaciens delivered T-DNA carrying the desired transgene BC into mature citrus cvs. 'Hamlin', 'Valencia' and 'Mid-Sweet' cells using this preconditioning method, resulting in transgenic scions expressing the transgene (FIGS. 5 and 6 and Table 5). These transgenic scions were grafted onto nontransgenic 'Carrizo' rootstock grown in soil from seeds. Transgenic mature citrus plants were obtained from Agrobacterium-mediated transformation experiments by this preconditioning method at a frequency of about half of the number of successfully grafted shoots. Successfully grafted shoots were obtained at frequencies ranging from 0.5% to 7% of the starting number of explants, which is comparable to the 0.6% to 12% frequencies obtained from use of Sinorhizobium in Example 8. The transgenic nature of roughly half of these citrus scion plants (0.25 to 3.5%) was confirmed by Western blots (FIGS. 5 and 6; some data not shown).

TABLE 5

*Agrobacterium* - mediated mature citrus scion transformation summary.

| | Experiment batch # | | | | | | | | | |
|---|---|---|---|---|---|---|---|---|---|---|
| | 12/21 | 12/21 | 01/19 | 11/17 | 11/22 | 03/28 | 03/28 | 04/11 | 05/02 | 05/02 |
| Mature cultivar | Ham | Val | Val | 'Mid-Sweet' | Ham | Ham | Val | Ham | Ham | Val |
| starting # explants | 84 | 187 | 100 | 80 | 65 | 220 | 129 | 128 | 180 | 160 |
| # explants with shoots on kanamycin | 9 (10%) | 30 (16%) | 4 (4%) | 8 (10%) | 7 (11%) | 15 (7%) | 11 (8.5%) | 19 (15%) | 28 (16%) | 25 (16%) |
| # grafted shoots | 6 (7%) | 12 (6%) | 5 (5%) | 2 (2.5%) | 4 (6%) | 4 (1%) | 6 (5%) | 3 (2%) | 1 (0.5%) | 2 (1.2%) |

Ham, 'Hamlin';
Val, 'Valencia'.

Unless defined otherwise, all technical and scientific terms herein have the same meaning as commonly understood by one of ordinary skill in the art to which this invention belongs. Definitions of common terms in molecular biology may be found in Benjamin Lewin, *Genes IX*, published by Oxford University Press, 2007 (ISBN-10 0131439812); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8); *Oxford Dictionary of Biochemistry and Molecular Biology*, Revised Edition, 2000. Although any methods and materials, similar or equivalent to those described herein, can be used in the practice or testing of the present invention, the preferred methods and materials are described herein.

Wherever methods are described and claimed, it should be understood that the methods of the present invention do not require that the listed procedures and/or steps of such methods necessarily must be performed exactly in the order indicated or that any one person or company necessarily must perform all of the steps themselves. For example, where a method has more than one procedure and/or step involved, the present invention contemplates that one individual or company may perform one or more of the procedures and/or steps of the method while another individual or company may perform one or more of the other procedures and/or steps of the same method. For example, in a method of preconditioning citrus internodal stem sections, one individual may produce, select and cultivate the callus from such sections while a different individual or company may conduct the transformation of the resultant calli.

All publications, patents, and patent publications cited are incorporated by reference herein in their entirety for all purposes. Also incorporated by reference herein are nucleic acid sequences and polypeptide sequences deposited into the GenBank, which are cited in this specification.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES CITED

Anderson, C. M., Castle, W. S., and Moore, G. A. 1991. Isozymic identification of zygotic seedlings in 'Swingle' Citrumelo Citrus paradisi X Poncirus trifoliata nursery and field populations. J. Amer. Soc. Hort. Sci. 116:322-326.

Broothaerts W, Mitchell H J, Weir B, Kaines S, Smith L M, Yang W, Mayer J E, Roa-Rodríguez C, Jefferson R A. 2005. Gene transfer to plants by diverse species of bacteria. Nature. 433:629-633

Chao, -C-C-T; Fang, -J-G; Devanand, -P-S. 2005. Long distance pollen flow in mandarin orchards determined by AFLP markers—implications for seedless mandarin production. J. Amer. Soc. Hort. Sci. 130: 374-380.

Cervera, M., Pina, J. A., Juarez, J., Navarro, L., and Pena, L. 1998. *Agrobacterium*-mediated transformation of citrange: factors affecting transformation and regeneration. PLANT CELL REP 18:271-278.

Cervera, M., Juarez, J., Navarro, A., Pina, J. A., Duran-Vila, N., Navarro, L., and Pena, L. 1998. Genetic transformation and regeneration of mature tissues of woody fruit plants bypassing the juvenile stage. Transgenic Research 7:51-59.

Cervera, M., Navarro, A., Navarro, L., and Pena, L. Production of transgenic adult plants from clementine mandarin by enhancing cell competence for transformation and regeneration. Tree Physiol. 28, 55-66. 2008.

Clark, J R. 1983. Age related changes in trees. J. Arboriculture 9:201-5.

Douglas C J, Halperin W, Nester E W (1982) *Agrobacterium tumefaciens* mutants affected in attachment to plant cells. J Bacteriol 152: 1265-1275

Frost H B (1943) Seed reproduction: development of gametes and embryos. In: Webber H J, Batchelor L D (eds) The Citrus industry, vol 1. University of California Press, Berkeley, Calif., pp 767-815.

Galibert, F. et al. 2001. The composite genome of the legume symbiont *Sinorhizobium meliloti*. Science 293: 668-672.

Garcia, R., Asins, M. J., Former, J., and Carbonell, E. A. 1999. Genetic analysis of apomixis in Citrus and Poncirus by molecular markers. Theoretical and Applied Genetics 99:511-518.

Gould J. H and M. Megallanes-Cedeno 1998 Adaptation of cotton shoot apex culture to *Agrobacterium* mediated transformation, Plant Mol. Biol. Rep. 16: 1-10

Kategari I. S, Vamadevaiah H. M, Udikeri S, Khadi B. M, Polumetla A. K 2007. Genetic transformation of an elite Indian genotype of cotton (*Gossypium hirsutum* L) for insect resistance Curr. Sci. 1843-1847

Koltunow, A. M., Soltys, K., Nito, N., and Mcclure, S. 1995. Anther, Ovule Seed, and Nucellar Embryo Development in Citrus-Sinensis Cv 'Valencia'. Canadian Journal of Botany—Revue Canadienne de Botanique 73:1567-1582.

Lazo, G. R., P. A. Stein, and R. A. Ludwig. 1991. A DNA transformation-competent *Arabidopsis* genomic library in *Agrobacterium*. Bio/Technology 9:963-967.

Lippincott B, Lippincott J A (1969) Bacterial attachment to a specific wound site as an essential stage in tumor initiation by *Agrobacterium tumefaciens*. J Bacteriol 97: 620-628

Long, S. 2001. Genes and Signals in the *Rhizobium*-Legume Symbiosis. Plant Physiol. 125:69-72.

Manner, H. I., R. S. Buker, V. Easton Smith, and C. R. Elevitch. 2006. Citrus species (citrus), ver. 2.1. In: Elevitch, C. R. (ed.). Species Profiles for Pacific Island Agroforestry. Permanent Agriculture Resources (PAR), Hôlualoa, Hawaii.

Miki and McHugh, 2004. Selectable marker genes in transgenic plants: applications, alternatives and biosafety. J. Biotechnol. 107:193-232.

Moore, G. A., Jacono, C. C., Neidigh, J. L., Lawrence, S. D. and Cline, K. Regeneration of transgenic plants. Plants Cell Rep. 11: 238-2542.

Moore, G. A. and Cline, K. 1987. Genetic transformation studies in *Citrus* using the *Agrobacterium tumefaciens* vector system. Annual Review Microbiology 22:1007.

Nogler G A (1984) Gametophytic apomixis. In: Jhri B M (ed) Embryology of angiosperms. Springer, Berlin Heidelberg New York, pp 475-518.

Peremyslov, V. V., Hagiwara, Y., and Dolja, V. V. 1999. HSP70 homolog functions in cell-to-cell movement of a plant virus. Proc. Natl. Acad. Sci. 96:14771-14776.

Pitzschke, A. and Hirt, H. 2010. New insights into an old story: *Agrobacterium*-induced tumour formation in plants by plant transformation. EMBO J. 29:1021-1032.

Slc, S and Gokceoglu, M 2007. Pollen analysis of honeys from Mediterranean region of Anatolia. Grana 46: 57-64

Spiegel-Roy, P and Goldschmidt, E E. (1996) pp 185-6 in Biology of Citrus. Cambridge University Press, 230 pp.

'Swingle', W T (1927) Seed production in sterile Citrus hybrids—its scientific explanation and practical significance. Hort. Soc. New York Mem. 3:19-21.

Wallace, H. M., King, B. J., and Lee, L. S. 2002. Pollen flow and the effect on fruit size in an 'Imperial' mandarin orchard. HortScience 37: 84-86.

Ward, J. E., Akiyoshi, D. E., Regier, D., Datta, A., Gordon, M. P and Nester, E. W., 1988. Characterization of the virB operon from an *Agrobacterium tumefaciens* Ti plasmid. J. Biol. Chem. 263:5804-5814.

Wendt, T., Doohan, F., Winckelmann, D. and Mullins, E., 2011. Gene transfer into *Solanum tuberosum* via *Rhizobium* spp. Transgenic Res. 20: 377-386.

Wood, D. W. et al. 2001. The genome of the natural genetic engineer *Agrobacterium tumefaciens* C58. Science 294: 2317-2323.

Zapata C, Srivalakanakul M, Park S. H, Lee B. M, Salas M. G Smith R. H (1999) Improvement in shoot apex regeneration of two fibre crops: cotton and Kenaf. *Plant Cell Tissue and Organ Cult.* 12: 43-50

---

The invention claimed is:

1. A method for transforming a mature citrus plant cell, comprising:
   (a) placing stem sections comprising mature citrus plant cells on a tissue culture medium suitable for formation of callus tissue;
   (b) selecting only those stem sections forming callus;
   (c) removing resulting callus from said selected stem sections;
   (d) contacting one or more of the mature citrus plant cells from said selected stem sections having had the callus removed with an *Agrobacterium* spp. or *Sinorhizobium* spp. bacterium comprising:
      (i) a first nucleic acid comprising a vir gene region of a Ti plasmid wherein the vir gene region acts to introduce a nucleic acid of interest into the plant cell in a VirD2-dependent manner; and
      (ii) a second nucleic acid comprising one or more T-DNA border sequence(s) operably linked to a nucleic acid of interest; and
   (e) selecting at least one transformed citrus plant cell comprising the nucleic acid of interest.

2. The method of claim 1, wherein the *Sinorhizobium* spp. bacterium is grown in the presence of a compound that enhances vir gene function prior to contacting the plant cell.

3. The method of claim 2, wherein the compound that enhances vir gene function is acetosyringone.

4. The method of claim 1, wherein the *Sinorhizobium* spp. bacterium is *Sinorhizobium* meliloti.

5. The method of claim 1, wherein the stem sections comprise internodal stem sections prepared from freshly emerging shoots of mature citrus plants.

6. The method of claim 1, wherein the stem sections comprise internodal stem sections prepared from first flushes of grafts of buds of mature plants onto rootstocks.

7. A method of enhancing transformation of a mature citrus plant cell, comprising:
   (a) placing stem sections comprising mature citrus plant cells on a tissue culture medium suitable for formation of callus tissue;
   (b) selecting only those stem sections forming callus;
   (c) removing resulting callus from said selected stem sections;
   (d) introducing a nucleic acid into one or more of the mature citrus plant cells from said selected stem sections having had the callus removed using *Agrobacterium* spp., or a non-*Agrobacterium* spp. Rhizobia cell, thereby producing a transformed cell comprising the nucleic acid; and
   (e) selecting at least one transformed citrus plant cell comprising the nucleic acid of interest.

8. The method of claim 7, wherein the stem sections comprising the plant cells are taken from freshly emerging shoots of mature citrus plants.

9. The method of claim 8, wherein the freshly emerging shoots of mature citrus are the first shoots from buds of mature plants following grafting onto rootstock.

10. The method of claim 7, wherein the transformed citrus plant cell is regenerated into a transgenic shoot by:
    (i) choosing a plant tissue comprising the transformed cell via selection and/or screening; and
    (ii) growing the chosen plant tissue under conditions that promote shoot elongation;
wherein the transformed citrus plant cell is regenerated into said transgenic shoot.

11. The method of claim 1, further comprising regenerating a citrus plant from the transformed citrus plant cell, wherein the regenerated citrus plant comprises the transformed nucleic acid.

12. The method of claim 1, further comprising regenerating a citrus plant from the transformed citrus plant cell by inducing the formation of a transformed citrus shoot from said transformed citrus plant cell, and grafting said transformed citrus shoot onto a rootstock, either transgenic or nontransgenic, wherein a graft union is formed, and the grafted shoot comprises the nucleic acid of interest.

13. A progeny plant of the citrus plant whether asexually or sexually reproduced, including all produce and seeds, plant tissues and plant parts transformed using the methods of claim 1.

14. The method of claim 1, wherein the *Agrobacterium* spp. bacterium is *Agrobacterium tumefaciens*.

* * * * *

SEQUENCE LISTING

```
<160> NUMBER OF SEQ ID NOS: 4

<210> SEQ ID NO 1
<211> LENGTH: 9917
<212> TYPE: DNA
<213> ORGANISM: Artificial Sequence
<220> FEATURE:
<223> OTHER INFORMATION: plasmid

<400> SEQUENCE: 1
ccgcctacat acctcgctct gctaatcctg ttaccagtgg ctgctgccag tggcgataag      60
tcgtgtctta ccggggttgga ctcaagacga tagttaccgg ataaggcgca gcggtcgggc     120
tgaacggggg gttcgtgcac acagcccagc ttggagcgaa cgacctacac cgaactgaga     180
tacctacagc gtgagctatg agaaagcgcc acgcttcccg aagggagaaa ggcggacagg     240
tatccggtaa gcggcagggt cggaacagga gagcgcacga gggagcttcc aggggaaac     300 gcctggtatc tttatagtcc tgtcgggttt cgccacctct gacttgagcg tcgattttg     360 tgatgctcgt caggggggcg gagcctatgg aaaaacgcca gcaacgcggc cttttacgg     420 ttcctggcct tttgctggcc ttttgctcac atgttctttc ctgcgttatc ccctgattct     480
gtggataacc gtattaccgc ctttgagtga gctgataccg ctcgccgcag ccgaacgacc     540
gagcgcagcg agtcagtgag cgaggaagcg gaagagcgcc tgatgcggta ttttctcctt     600
acgcatctgt gcggtatttc acaccgcata tggtgcactc tcagtacaat ctgctctgat     660
gccgcatagt taagccagta tacactccgc tatcgctacg tgactgggtc atggctgcgc     720
cccgacaccc gccaacaccc gctgacgcgc cctgacgggc ttgtctgctc ccggcatccg     780
cttacagaca agctgtgacc gtctccggga gctgcatgtg tcagaggttt tcaccgtcat     840
```

```
caccgaaacg cgcgaggcag ggtgccttga tgtgggcgcc ggcggtcgag tggcgacggc    900
gcggcttgtc cgcgccctgg tagattgcct ggccgtaggc cagccatttt tgagcggcca    960
gcggccgcga taggccgacg cgaagcggcg gggcgtaggg agcgcagcga ccgaagggta   1020
ggcgcttttt gcagctcttc ggctgtgcgc tggccagaca gttatgcaca ggccaggcgg   1080
gttttaagag ttttaataag ttttaaagag ttttaggcgg aaaaatcgcc ttttttctct   1140
tttatatcag tcacttacat gtgtgaccgg ttcccaatgt acggctttgg gttcccaatg   1200
tacgggttcc ggttcccaat gtacggcttt gggttcccaa tgtacgtgct atccacagga   1260
aagagacctt ttcgaccttt ttcccctgct agggcaattt gccctagcat ctgctccgta   1320
cattaggaac cggcggatgc ttcgccctcg atcaggttgc ggtagcgcat gactaggatc   1380
gggccagcct gccccgcctc ctccttcaaa tcgtactccg gcaggtcatt tgacccgatc   1440
agcttgcgca cggtgaaaca gaacttcttg aactctccgg cgctgccact gcgttcgtag   1500
atcgtcttga caaccatct ggcttctgcc ttgcctgcgg cgcggcgtgc caggcggtag   1560
agaaaacggc cgatgccggg atcgatcaaa agtaatcgg ggtgaaccgt cagcacgtcc   1620
gggttcttgc cttctgtgat ctcgcggtac atccaatcag ctagctcgat ctcgatgtac   1680
tccggccgcc cggtttcgct cttttacgatc ttgtagcggc taatcaaggc ttcaccctcg   1740
gataccgtca ccaggcggcc gttcttggcc ttcttcgtac gctgcatggc aacgtgcgtg   1800
gtgtttaacc gaatgcaggt ttctaccagg tcgtctttct gctttccgcc atcggctcgc   1860
cggcagaact tgagtacgtc cgcaacgtgt ggacggaaca cgcggccggg cttgtctccc   1920
ttcccttccc ggtatcggtt catggattcg gttagatggg aaaccgccat cagtaccagg   1980
tcgtaatccc acacactggc catgccggcc gggcctgcgg aaacctctac gtgcccgtct   2040
ggaagctcgt agcggatcac ctcgccagct cgtcggtcac gcttcgacag acggaaaacg   2100
gccacgtcca tgatgctgcg actatcgcgg gtgcccacgt catagagcat cggaacgaaa   2160
aaatctggtt gctcgtcgcc cttgggcggc ttcctaatcg acggcgcacc ggctgccggc   2220
ggttgccggg attctttgcg gattcgatca gcggccgctt gccacgattc accggggcgt   2280
gcttctgcct cgatgcgttg ccgctgggcg gcctgcgcgg ccttcaactt ctccaccagg   2340
tcatcaccca gcgccgcgcc gatttgtacc gggccggatg gtttgcgacc gtcacgccga   2400
ttcctcgggc ttgggggttc cagtgccatt gcaggccgg cagacaaccc agccgcttac   2460
gcctggccaa ccgcccgttc ctccacacat ggggcattcc acggcgtcgg tgcctggttg   2520
ttcttgattt tccatgccgc ctccttttagc cgctaaaatt catctactca tttattcatt   2580
tgctcattta ctctggtagc tgcgcgatgt attcagatag cagctcggta atggtcttgc   2640
cttggcgtac cgcgtacatc ttcagcttgg tgtgatcctc cgccggcaac tgaaagttga   2700
cccgcttcat ggctggcgtg tctgccaggc tggccaacgt tgcagccttg ctgctgcgtg   2760
cgctcggacg gccggcactt agcgtgtttg tgcttttgct catttctctc ttacctcatt   2820
aactcaaatg agttttgatt taatttcagc ggccagcgcc tggacctcgc gggcagcgtc   2880
gccctcgggt tctgattcaa gaacggttgt gccggcggcg gcagtgcctg ggtagctcac   2940
gcgctgcgta atacgggact caagaatggg cagctcgtac ccggccagcg cctcggcaac   3000
ctcaccgccg atgcgcgtgc ctttgatcgc ccgcgacacg acaaaggccg cttgtagcct   3060
tccatccgtg acctcaatgc gctgcttaac cagctccacc aggtcggcgg tggcccatat   3120
gtcgtaaggg cttggctgca ccggaatcag cacgaagtcg gctgccttga tcgcggacac   3180
agccaagtcc gccgcctggg gcgctccgtc gatcactacg aagtcgcgcc ggccgatggc   3240
```

```
cttcacgtcg cggtcaatcg tcgggcggtc gatgccgaca acggttagcg gttgatcttc    3300
ccgcacggcc gcccaatcgc gggcactgcc ctggggatcg gaatcgacta acagaacatc    3360
ggccccggcg agttgcaggg cgcgggctag atgggttgcg atggtcgtct tgcctgaccc    3420
gcctttctgg ttaagtacag cgataacctt catgcgttcc ccttgcgtat ttgtttattt    3480
actcatcgca tcatatacgc agcgaccgca tgacgcaagc tgttttactc aaatacacat    3540
caccttttta gacggcggcg ctcggtttct tcagcggcca agctggccgg ccaggccgcc    3600
agcttggcat cagacaaacc ggccaggatt tcatgcagcc gcacggttga gacgtgcgcg    3660
ggcggctcga acacgtaccc ggccgcgatc atctccgcct cgatctcttc ggtaatgaaa    3720
aacggttcgt cctggccgtc ctggtgcggt ttcatgcttg ttcctcttgg cgttcattct    3780
cggcggccgc cagggcgtcg gcctcggtca atgcgtcctc acggaaggca ccgcgccgcc    3840
tggcctcggt gggcgtcact tcctcgctgc gctcaagtgc gcggtacagg gtcgagcgat    3900
gcacgccaag cagtgcagcc gcctctttca cggtgcggcc ttcctggtcg atcagctcgc    3960
gggcgtgcgc gatctgtgcc ggggtgaggg tagggcgggg gccaaacttc acgcctcggg    4020
ccttggcggc ctcgcgcccg ctccgggtgc ggtcgatgat tagggaacgc tcgaactcgg    4080
caatgccggc gaacacggtc aacaccatgc ggccggccgg cgtggtggtg tcggcccacg    4140
gctctgccag gctacgcagg cccgcgccgg cctcctggat gcgctcggca atgtccagta    4200
ggtcgcgggt gctgcgggcc aggcggtcta gcctggtcac tgtcacaacg tcgccagggc    4260
gtaggtggtc aagcatcctg gccagctccg ggcggtcgcg cctggtgccg gtgatcttct    4320
cggaaaacag cttggtgcag ccggccgcgt gcagttcggc ccgttggttg gtcaagtcct    4380
ggtcgtcggt gctgacgcgg gcatagccca gcaggccagc ggcggcgctc ttgttcatgg    4440
cgtaatgtct ccggttctag tcgcaagtat tctactttat gcgactaaaa cacgcgacaa    4500
gaaaacgcca ggaaagggc agggcggcag cctgtcgcgt aacttaggac ttgtgcgaca    4560
tgtcgttttc agaagacggc tgcactgaac gtcagaagcc gactgcacta tagcagcgga    4620
ggggttggat caaagtactt tgatcccgag gggaaccctg tggttggcat gcacatacaa    4680
atggacgaac ggataaacct tttcacgccc ttttaaatat ccgttattct aataaacgct    4740
cttttctctt aggtttaccc gccaatatat cctgtcaaac actgatagtt taattcccga    4800
tctagtaaca tagatgacac cgcgcgcgat aatttatcct agtttgcgcg ctatattttg    4860
ttttctatcg cgtattaaat gtataattgc gggactctaa tcataaaaac ccatctcata    4920
aataacgtca tgcattacat gttaattatt acatgcttaa cgtaattcaa cagaaattat    4980
atgataatca tcgcaagacc ggcaacagga ttcaatctta agaaacttta ttgccaaatg    5040
tttgaacgat cggggaaatt cgagctggtc acctgtaatt cacacgtggt ggtggtggtg    5100
gtggctagcg ttaacactag tctagattat gacaaaagag agtcgccatc agctgctgga    5160 gggtctgca cctcaccagc ttcggcaggc ttttcctttt tcttccttct atttccgccg    5220
ccagcctgag caacttctcc ctcagcagtc ttggcgttct ggcctctagc tgatgcccta    5280
acctgctcga atgcagcaga ctcttcggca gtagcaacag ggaggttctg aagctcttca    5340
atcaaggcat cagcaccaac tggatgtctc ttaagccact cgatgccatc agccttctgg    5400
gcttcggtag gcttgaaatc tgctgtaacg taagcgaagt tcctgttctt tctgatgtca    5460
tcaatcttac caactgtagt gccaagagca tcggctgcag ccttagttgt ggtagttgac    5520
tgagagccga atcttgcaag agctacaact gcgataggca ttctaccacg gataatttct    5580
```

```
tttggaggag ccttctcggc aggagtggtc tgggtggtat cggtctgatc agatgcactg  5640
gtggtaccaa tgctaaggag gacaaggatg gcaagagcct gcagaattaa tcaattacac  5700
acgaaataaa gtaatcagat tatcagttaa agctatgtaa tatttacacc ataaccaatc  5760
aattaaaaaa tagatcagtt taaaaacaga tcgaagctca aaaaaataaa agagaaaag   5820 ggtcctaacc aagaaaatga aggagaaaaa ctagaaattt acctgcagat gcttagtagt  5880
agccatggtc aagagtcccc cgtgttctct ccaaatgaaa tgaacttcct tatatagagg  5940
aagggtcttg cgaaggatag tgggattgtg cgtcatccct tacgtcagtg gagatatcac  6000
atcaatccac ttgctttgaa gacgtggttg gaacgtcttc ttttccacg  atgctcctcg  6060 tgggtggggg tccatctttg ggaccactgt cggcagaggc atcttcaacg atggcctttc  6120
ctttatcgca atgatggcat ttgtaggagc caccttcctt ttccactatc ttcacaataa  6180
agtgacagat agctgggcaa tggaatccga ggaggtttcc ggatattacc ctttgttgaa  6240
aagtctcaat tgccctttgg tcttctgaga ctgtatcttt gatattttg  gagtagacaa  6300 gtgtgtcgtg ctccaccatg ttgacgaaga ttttcttctt gtcattgagt cgtaagagac  6360
tctgtatgaa ctgttcgcca gtctttacgg cgagttctgt taggtcctct atttgaatct  6420
ttgactccat gaagctaaac tgaaggcggg aaacgacaat ctgatccaag ctcaagctgc  6480
tctagcattc gccattcagg ctgcgcaact gttgggaagg gcgatcggtg cgggcctctt  6540
cgctattacg ccagctggcg aaaggggat  gtgctgcaag gcgattaagt tgggtaacgc  6600
cagggttttc ccagtcacga cgttgtaaaa cgacggccag tgccaagctt ggaaactgaa  6660
ggcgggaaac gacaatctga tcatgagcgg agaattaagg gagtcacgtt atgaccccg   6720 ccgatgacgc gggacaagcc gttttacgtt tggaactgac agaaccgcaa cgattgaagg  6780
agccactcag ccgcgggttt ctggagttta atgagctaag cacatacgtc agaaaccatt  6840
attgcgcgtt caaaagtcgc ctaaggtcac tatcagctag caaatatttc ttgtcaaaaa  6900
tgctccactg acgttccata aattcccctc ggtatccaat tagagtctca tattcactct  6960
caatccaaat aatctgcacc ggatctggat cgtttcgcat gattgaacaa gatggattgc  7020
acgcaggttc tccggccgct tgggtggaga ggctattcgg ctatgactgg gcacaacaga  7080
caatcggctg ctctgatgcc gccgtgttcc ggctgtcagc gcaggggcgc ccggttcttt  7140
ttgtcaagac cgacctgtcc ggtgccctga atgaactgca ggacgaggca gcgcggctat  7200
cgtggctggc cacgacgggc gttccttgcg cagctgtgct cgacgttgtc actgaagcgg  7260
gaagggactg gctgctattg ggcgaagtgc cggggcagga tctcctgtca tctcaccttg  7320
ctcctgccga gaaagtatcc atcatggctg atgcaatgcg gcggctgcat acgcttgatc  7380
cggctacctg cccattcgac caccaagcga aacatcgcat cgagcgagca cgtactcgga  7440
tggaagccgg tcttgtcgat caggatgatc tggacgaaga gcatcagggg ctcgcgccag  7500
ccgaactgtt cgccaggctc aaggcgcgca tgcccgacgg cgatgatctc gtcgtgaccc  7560
atggcgatgc ctgcttgccg aatatcatgg tggaaaatgg ccgcttttct ggattcatcg  7620
actgtggccg gctgggtgtg gcggaccgct atcaggacat agcgttggct acccgtgata  7680
ttgctgaaga gcttggcggc gaatgggctg accgcttcct cgtgctttac ggtatcgccg  7740
ctcccgattc gcagcgcatc gccttctatc gccttcttga cgagttcttc tgagcgggac  7800 tctgggttc  ggatcgatcc tctagctaga gtcgatcgac aagctcgagt ttctccataa  7860
taatgtgtga gtagttccca gataagggaa ttagggttcc tatagggttt cgctcatgtg  7920
ttgagcatat aagaaaccct tagtatgtat ttgtatttgt aaaatacttc tatcaataaa  7980
```

```
atttctaatt cctaaaacca aaatccagta ctaaaatcca gatcccccga attaattcgg      8040
cgttaattca gtacattaaa aacgtccgca atgtgttatt aagttgtcta agcgtcaatt      8100
tgtttacacc acaatatatc ctgccaccag ccagccaaca gctccccgac cggcagctcg      8160
gcacaaaatc accactcgat acaggcagcc catcagtccg ggacggcgtc agcgggagag      8220
ccgttgtaag gcggcagact ttgctcatgt taccgatgct attcggaaga acggcaacta      8280
agctgccggg tttgaaacac ggatgatctc gcggagggta gcatgttgat tgtaacgatg      8340
acagagcgtt gctgcctgtg atcaccgcgg atgacagagc gttgctgcct gtgatcaatt      8400
cgggcacgaa cccagtggac ataagcctcg ttcggttcgt aagctgtaat gcaagtagcg      8460
taactgccgt cacgcaactg gtccagaacc ttgaccgaac gcagcggtgg taacggcgca      8520
gtggcggttt tcatggcttc ttgttatgac atgtttttt ggggtacagt ctatgcctcg      8580
ggcatccaag cagcaagcgc gttacgccgt gggtcgatgt ttgatgttat ggagcagcaa      8640
cgatgttacg cagcagggca gtcgccctaa aacaaagtta aacatcatgg gggaagcggt      8700
gatcgccgaa gtatcgactc aactatcaga ggtagttggc gtcatcgagc gccatctcga      8760
accgacgttg ctggccgtac atttgtacgg ctccgcagtg gatggcggcc tgaagccaca      8820
cagtgatatt gatttgctgg ttacggtgac cgtaaggctt gatgaaacaa cgcggcgagc      8880
tttgatcaac gacctttggg aaacttcggc ttcccctgga gagagcgaga ttctccgcgc      8940
tgtagaagtc accattgttg tgcacgacga catcattccg tggcgttatc cagctaagcg      9000
cgaactgcaa tttggagaat ggcagcgcaa tgacattctt gcaggtatct tcgagccagc      9060
cacgatcgac attgatctgg ctatcttgct gacaaaagca agagaacata gcgttgcctt      9120
ggtaggtcca gcggcggagg aactctttga tccggttcct gaacaggatc tatttgaggc      9180
gctaaatgaa accttaacgc tatggaactc gccgcccgac tgggctggcg atgagcgaaa      9240
tgtagtgctt acgttgtccc gcatttggta cagcgcagta accggcaaaa tcgcgccgaa      9300
ggatgtcgct gccgactggg caatggagcg cctgccggcc cagtatcagc ccgtcatact      9360
tgaagctaga caggcttatc ttggacaaga agaagatcgc ttggcctcgc gcgcagatca      9420
gttggaagaa tttgtccact acgtgaaagg cgagatcacc aaggtagtcg gcaaataatg      9480
tctagctaga aattcgttca agccgacgcc gcttcgccgg cgttaactca agcgattaga      9540
tgcactaagc acataattgc tcacagccaa actatcaggt caagtctgct tttattattt      9600
ttaagcgtgc ataataagcc ctacacaaat tgggagatat atcatgcatg accaaaatcc      9660
cttaacgtga gtttcgttc cactgagcgt cagaccccgt agaaaagatc aaaggatctt      9720
cttgagatcc ttttttttctg cgcgtaatct gctgcttgca acaaaaaaa ccaccgctac      9780 cagcggtggt ttgtttgccg gatcaagagc taccaactct ttttccgaag gtaactggct      9840
tcagcagagc gcagatacca aatactgtcc ttctagtgta gccgtagtta ggccaccact      9900
tcaagaactc tgtagca                                                    9917
```

<210> SEQ ID NO 2
<211> LENGTH: 8952
<212> TYPE: DNA
<213> ORGANISM: Artificial Sequence
<220> FEATURE:
<223> OTHER INFORMATION: plasmid

<400> SEQUENCE: 2

```
gttaacgcta gccaccacca ccaccaccac gtgtgaatta caggtgacca gctcgaattt       60
```

```
ccccgatcgt tcaaacattt ggcaataaag tttcttaaga ttgaatcctg ttgccggtct    120
tgcgatgatt atcatataat ttctgttgaa ttacgttaag catgtaataa ttaacatgta    180
atgcatgacg ttatttatga gatgggtttt tatgattaga gtcccgcaat tatacattta    240
atacgcgata gaaaacaaaa tatagcgcgc aaactaggat aaattatcgc gcgcggtgtc    300
atctatgtta ctagatcggg aattaaacta tcagtgtttg acaggatata ttggcgggta    360
aacctaagag aaaagagcgt ttattagaat aacggatatt taaagggcg tgaaaaggtt    420 tatccgttcg tccatttgta tgtgcatgcc aaccacaggg ttcccctcgg gatcaaagta    480
ctttgatcca acccctccgc tgctatagtg cagtcggctt ctgacgttca gtgcagccgt    540
cttctgaaaa cgacatgtcg cacaagtcct aagttacgcg acaggctgcc gccctgccct    600
tttcctggcg ttttcttgtc gcgtgtttta gtcgcataaa gtagaatact tgcgactaga    660
accggagaca ttacgccatg aacaagagcg ccgccgctgg cctgctgggc tatgcccgcg    720
tcagcaccga cgaccaggac ttgaccaacc aacgggccga actgcacgcg gccggctgca    780
ccaagctgtt ttccgagaag atcaccggca ccaggcgcga ccgcccggag ctggccagga    840
tgcttgacca cctacgccct ggcgacgttg tgacagtgac caggctagac cgcctggccc    900
gcagcacccg cgacctactg gacattgccg agcgcatcca ggaggccggc gcgggcctgc    960
gtagcctggc agagccgtgg gccgacacca ccacgccggc cggccgcatg gtgttgaccg   1020
tgttcgccgg cattgccgag ttcgagcgtt ccctaatcat cgaccgcacc ggagcgggc    1080 gcgaggccgc caaggcccga ggcgtgaagt ttggcccccg ccctaccctc accccggcac   1140
agatcgcgca cgcccgcgag ctgatcgacc aggaaggccg caccgtgaaa gaggcggctg   1200
cactgcttgg cgtgcatcgc tcgaccctgt accgcgcact tgagcgcagc gaggaagtga   1260
cgcccaccga ggccaggcgg cgcggtgcct tccgtgagga cgcattgacc gaggccgacg   1320
ccctggcggc cgccgagaat gaacgccaag aggaacaagc atgaaaccgc accaggacgg   1380
ccaggacgaa ccgttttttca ttaccgaaga gatcgaggcg gagatgatcg cggccgggta   1440
cgtgttcgag ccgcccgcgc acgtctcaac cgtgcggctg catgaaatcc tggccggttt   1500
gtctgatgcc aagctggcgg cctggccggc cagcttggcc gctgaagaaa ccgagcgccg   1560
ccgtctaaaa aggtgatgtg tatttgagta aaacagcttg cgtcatgcgg tcgctgcgta   1620
tatgatgcga tgagtaaata aacaaatacg caaggggaac gcatgaaggt tatcgctgta   1680
cttaaccaga aaggcgggtc aggcaagacg accatcgcaa cccatctagc ccgcgccctg   1740
caactcgccg gggccgatgt tctgttagtc gattccgatc cccagggcag tgcccgcgat   1800
tgggcggccg tgcgggaaga tcaaccgcta accgttgtcg gcatcgaccg cccgacgatt   1860
gaccgcgacg tgaaggccat cggccggcgc gacttcgtag tgatcgacgg agcgccccag   1920
gcggcggact tggctgtgtc cgcgatcaag gcagccgact tcgtgctgat tccggtgcag   1980
ccaagccctt acgacatatg gccaccgccg gacctggtgg agctggttaa gcagcgcatt   2040
gaggtcacgg atgaaggct acaagcggcc tttgtcgtgt cgcgggcgat caaaggcacg   2100
cgcatcggcg gtgaggttgc cgaggcgctg gccgggtacg agctgcccat tcttgagtcc   2160
cgtatcacgc agcgcgtgag ctacccaggc actgccgccg ccggcacaac cgttcttgaa   2220
tcagaacccg agggcgacgc tgcccgcgag gtccaggcgc tggccgctga aattaaatca   2280
aaactcattt gagttaatga ggtaaagaga aaatgagcaa aagcacaaac acgctaagtg   2340
ccggccgtcc gagcgcacgc agcagcaagg ctgcaacgtt ggccagcctg cagacacgc    2400 cagccatgaa gcgggtcaac tttcagttgc cggcggagga tcacaccaag ctgaagatgt   2460
```

```
acgcggtacg ccaaggcaag accattaccg agctgctatc tgaatacatc gcgcagctac  2520
cagagtaaat gagcaaatga ataaatgagt agatgaattt tagcggctaa aggaggcggc  2580
atggaaaatc aagaacaacc aggcaccgac gccgtggaat gccccatgtg tggaggaacg  2640
ggcggttggc caggcgtaag cggctgggtt gtctgccggc cctgcaatgg cactggaacc  2700
cccaagcccg aggaatcggc gtgacggtcg caaaccatcc ggcccggtac aaatcggcgc  2760
ggcgctgggt gatgacctgg tggagaagtt gaaggccgcg caggccgccc agcggcaacg  2820
catcgaggca gaagcacgcc ccggtgaatc gtggcaagcg gccgctgatc gaatccgcaa  2880
agaatcccgg caaccgccgg cagccggtgc gccgtcgatt aggaagccgc caagggcga  2940 cgagcaacca gattttttcg ttccgatgct ctatgacgtg ggcacccgcg atagtcgcag  3000
catcatggac gtggccgttt ccgtctgtc gaagcgtgac cgacgagctg gcgaggtgat  3060
ccgctacgag cttccagacg ggcacgtaga ggtttccgca gggccggccg gcatggccag  3120
tgtgtgggat tacgacctgg tactgatggc ggttccccat ctaaccgaat ccatgaaccg  3180
ataccgggaa gggaagggag acaagcccgg ccgcgtgttc cgtccacacg ttgcggacgt  3240
actcaagttc tgccggcgag ccgatggcgg aaagcagaaa gacgacctgg tagaaacctg  3300
cattcggtta acaccacgc acgttgccat gcagcgtacg aagaaggcca agaacggccg  3360
cctggtgacg gtatccgagg gtgaagcctt gattagccgc tacaagatcg taaagagcga  3420
aaccgggcgg ccggagtaca tcgagatcga gctagctgat tggatgtacc gcgagatcac  3480
agaaggcaag aacccggacg tgctgacggt tcaccccgat tactttttga tcgatcccgg  3540
catcggccgt tttctctacc gcctggcacg ccgcgccgca ggcaaggcag aagccagatg  3600
gttgttcaag acgatctacg aacgcagtgg cagcgccgga gagttcaaga agttctgttt  3660
caccgtgcgc aagctgatcg ggtcaaatga cctgccggag tacgatttga aggaggaggc  3720
ggggcaggct ggcccgatcc tagtcatgcg ctaccgcaac ctgatcgagg gcgaagcatc  3780
cgccggttcc taatgtacgg agcagatgct agggcaaatt gccctagcag gggaaaaagg  3840
tcgaaaaggt ctctttcctg tggatagcac gtacattggg aacccaaagc cgtacattgg  3900
gaaccggaac ccgtacattg ggaacccaaa gccgtacatt gggaaccggt cacacatgta  3960
agtgactgat ataaaagaga aaaaggcga ttttttccgcc taaaactctt taaaacttat  4020
taaaactctt aaaacccgcc tggcctgtgc ataactgtct ggccagcgca cagccgaaga  4080
gctgcaaaaa gcgcctaccc ttcggtcgct gcgctcccta cgccccgccg cttcgcgtcg  4140
gcctatcgcg gccgctggcc gctcaaaaat ggctggccta cggccaggca atctaccagg  4200
gcgcggacaa gccgcgccgt cgccactcga ccgccggcgc ccacatcaag gcaccctgcc  4260
tcgcgcgttt cggtgatgac ggtgaaaacc tctgacacat gcagctcccg gagacggtca  4320
cagcttgtct gtaagcggat gccgggagca gacaagcccg tcagggcgcg tcagcgggtg  4380
ttggcgggtg tcgggcgca gccatgaccc agtcacgtag cgatagcgga gtgtatactg  4440
gcttaactat gcggcatcag agcagattgt actgagagtg caccatatgc ggtgtgaaat  4500
accgcacaga tgcgtaagga gaaaataccg catcaggcgc tcttccgctt cctcgctcac  4560
tgactcgctg cgctcggtcg ttcggctgcg gcgagcggta tcagctcact caaaggcggt  4620
aatacggtta tccacagaat caggggataa cgcaggaaag aacatgtgag caaaaggcca  4680
gcaaaaggcc aggaaccgta aaaaggccgc gttgctggcg ttttttccata ggctccgccc  4740 ccctgacgag catcacaaaa atcgacgctc aagtcagagg tggcgaaacc cgacaggact  4800
```

```
ataaagatac caggcgtttc cccctggaag ctccctcgtg cgctctcctg ttccgaccct    4860
gccgcttacc ggatacctgt ccgcctttct cccttcggga agcgtggcgc tttctcatag    4920
ctcacgctgt aggtatctca gttcggtgta ggtcgttcgc tccaagctgg gctgtgtgca    4980 cgaaccccccc gttcagcccg accgctgcgc cttatccggt aactatcgtc ttgagtccaa    5040
cccggtaaga cacgacttat cgccactggc agcagccact ggtaacagga ttagcagagc    5100
gaggtatgta ggcggtgcta cagagttctt gaagtggtgg cctaactacg gctacactag    5160
aaggacagta tttggtatct gcgctctgct gaagccagtt accttcggaa aaagagttgg    5220
tagctcttga tccggcaaac aaaccaccgc tggtagcggt ggttttttg tttgcaagca    5280 gcagattacg cgcagaaaaa aaggatctca agaagatcct ttgatctttt ctacggggtc    5340
tgacgctcag tggaacgaaa actcacgtta agggattttg gtcatgcatt ctaggtacta    5400
aaacaattca tccagtaaaa tataatattt tattttctcc caatcaggct tgatcccag    5460 taagtcaaaa aatagctcga catactgttc ttccccgata tcctccctga tcgaccggac    5520
gcagaaggca atgtcatacc acttgtccgc cctgccgctt ctcccaagat caataaagcc    5580
acttactttg ccatctttca caaagatgtt gctgtctccc aggtcgccgt gggaaaagac    5640
aagttcctct tcgggctttt ccgtctttaa aaaatcatac agctcgcgcg gatctttaaa    5700
tggagtgtct tcttcccagt tttcgcaatc cacatcggcc agatcgttat tcagtaagta    5760
atccaattcg gctaagcggc tgtctaagct attcgtatag gacaatccg atatgtcgat    5820 ggagtgaaag agcctgatgc actccgcata cagctcgata tcttttcag ggctttgttc    5880 atcttcatac tcttccgagc aaaggacgcc atcggcctca ctcatgagca gattgctcca    5940
gccatcatgc cgttcaaagt gcaggacctt tggaacaggc agctttcctt ccagccatag    6000
catcatgtcc ttttcccgtt ccacatcata ggtggtccct ttataccggc tgtccgtcat    6060 tttaaatat aggttttcat tttctcccac cagcttatat accttagcag gagacattcc    6120
ttccgtatct tttacgcagc ggtatttttc gatcagtttt ttcaattccg gtgatattct    6180
cattttagcc atttattatt ccttcctct tttctacagt atttaaagat accccaagaa    6240
gctaattata caagacgaa ctccaattca ctgttccttg cattctaaaa ccttaaatac    6300
cagaaaacag ctttttcaaa gttgttttca agttggcgt ataacatagt atcgacggag    6360
ccgattttga aaccgcggtg atcacaggca gcaacgctct gtcatcgtta caatcaacat    6420
gctaccctcc gcgagatcat ccgtgtttca aacccggcag cttagttgcc gttcttccga    6480
atagcatcgg taacatgagc aaagtctgcc gccttacaac ggctctcccg ctgacgccgt    6540
cccggactga tgggctgcct gtatcgagtg gtgattttgt gccgagctgc cggtcgggga    6600
gctgttggct ggctggtggc aggatatatt gtggtgtaaa caaattgacg cttagacaac    6660
ttaataacac attgcggacg ttttttaatgt actgaattaa cgccgaatta attcggggga    6720
tctggatttt agtactggat tttggtttta ggaattagaa attttattga tagaagtatt    6780
ttacaaatac aaatacatac taagggtttc ttatatgctc aacacatgag cgaaaccta    6840 taggaaccct aattccctta tctgggaact actcacacat tattatggag aaactcgagc    6900
ttgtcgatcg actctagcta gaggatcgat ccgaacccca gagtcccgct cagaagaact    6960
cgtcaagaag gcgatagaag gcgatgcgct gcgaatcggg agcggcgata ccgtaaagca    7020
cgaggaagcg gtcagcccat tcgccgccaa gctcttcagc aatatcacgg gtagccaacg    7080
ctatgtcctg atagcggtcc gccacaccca gccggccaca gtcgatgaat ccagaaaagc    7140
ggccattttc caccatgata ttcggcaagc aggcatcgcc atgggtcacg acgagatcat    7200
```

```
cgccgtcggg catgcgcgcc ttgagcctgg cgaacagttc ggctggcgcg agccctgat    7260 gctcttcgtc cagatcatcc tgatcgacaa gaccggcttc catccgagta cgtgctcgct    7320
cgatgcgatg tttcgcttgg tggtcgaatg ggcaggtagc cggatcaagc gtatgcagcc    7380
gccgcattgc atcagccatg atggatactt tctcggcagg agcaaggtga gatgacagga    7440
gatcctgccc cggcacttcg cccaatagca gccagtccct tcccgcttca gtgacaacgt    7500
cgagcacagc tgcgcaagga acgcccgtcg tggccagcca cgatagccgc gctgcctcgt    7560
cctgcagttc attcagggca ccggacaggt cggtcttgac aaaaagaacc gggcgcccct    7620
gcgctgacag ccggaacacg gcggcatcag agcagccgat tgtctgttgt gcccagtcat    7680
agccgaatag cctctccacc caagcggccg gagaacctgc gtgcaatcca tcttgttcaa    7740
tcatgcgaaa cgatccagat ccggtgcaga ttatttggat tgagagtgaa tatgagactc    7800
taattggata ccgaggggaa tttatggaac gtcagtggag cattttgac aagaaatatt    7860 tgctagctga tagtgacctt aggcgacttt tgaacgcgca ataatggttt ctgacgtatg    7920
tgcttagctc attaaactcc agaaacccgc ggctgagtgg ctccttcaat cgttgcggtt    7980
ctgtcagttc caaacgtaaa acggcttgtc ccgcgtcatc ggcggggtc ataacgtgac    8040 tcccttaatt ctccgctcat gatcagattg tcgtttcccg ccttcagttt ccaagcttcg    8100
atatcattga tagagcagtc tcttcgtcgg tcgacgggaa gatcgtcagt cttttcgacc    8160
tcggtcgtct tagttaacac agttactaag gttccatttt attattgcat tgtttttcat    8220
ttagtgtaat cgtacttgag ttctaacatg tctgatcaga ccgataccac ccagaccact    8280
cctgccgaga aggctcctcc aaaagaaatt atcagggta gaatgcctat cgcagttgta    8340
gctcttgcaa gattcggctc tcagtcaact accacaacta aggctgcagg taaatttcta    8400 gttttctcc ttcattttct tggttaggac ccttttctct tttattttt ttgagcttcg    8460 atctgttttt aaactgatct atttttaat tgattggtta tggtgtaaat attacatagc    8520
tttaactgat aatctgatta ctttatttcg tgtgtaattg attaattctg cagccgatgc    8580
tcttggcact acagttggta agattgatga catcagaaag aacaggaact tcgcttacgt    8640
tacagcagat ttcaagccta ccgaagccca gaaggctgat ggcatcgagt ggcttaagag    8700
acatccagtt ggtgctgatg ccttgattga agagcttcag aacctccctg ttgctactgc    8760
cgaagagtct gctgcattcg agcaggttag ggcatcagct agaggccaga acgccaagac    8820
tgctgaggga gaagttgctc aggctggcgg cggaaataga aggaagaaaa aggaaaagcc    8880
tgccgaagct ggtgaggtgc agaaccctcc agcagctgat ggcgactctc ttttgtcata    8940
atctagacta gt                                                         8952
```

<210> SEQ ID NO 3
<211> LENGTH: 9561
<212> TYPE: DNA
<213> ORGANISM: Artificial Sequence
<220> FEATURE:
<223> OTHER INFORMATION: plasmid

<400> SEQUENCE: 3

```
gttaacgcta gccaccacca ccaccaccac gtgtgaatta caggtgacca gctcgaattt     60
ccccgatcgt tcaaacattt ggcaataaag tttcttaaga ttgaatcctg ttgccggtct    120
tgcgatgatt atcatataat ttctgttgaa ttacgttaag catgtaataa ttaacatgta    180
atgcatgacg ttatttatga gatgggtttt tatgattaga gtcccgcaat tatacattta    240
```

```
atacgcgata gaaaacaaaa tatagcgcgc aaactaggat aaattatcgc gcgcggtgtc   300
atctatgtta ctagatcggg aattaaacta tcagtgtttg acaggatata ttggcgggta   360
aacctaagag aaaagagcgt ttattagaat aacggatatt taaaagggcg tgaaaaggtt   420
tatccgttcg tccatttgta tgtgcatgcc aaccacaggg ttcccctcgg gatcaaagta   480
ctttgatcca accccctccgc tgctatagtg cagtcggctt ctgacgttca gtgcagccgt   540
cttctgaaaa cgacatgtcg cacaagtcct aagttacgcg acaggctgcc gccctgccct   600
tttcctggcg ttttcttgtc gcgtgtttta gtcgcataaa gtagaatact tgcgactaga   660
accggagaca ttacgccatg aacaagagcg ccgccgctgg cctgctgggc tatgcccgcg   720
tcagcaccga cgaccaggac ttgaccaacc aacgggccga actgcacgcg gccggctgca   780
ccaagctgtt ttccgagaag atcaccggca ccaggcgcga ccgcccggag ctggccagga   840
tgcttgacca cctacgccct ggcgacgttg tgacagtgac caggctagac cgcctggccc   900
gcagcacccg cgacctactg gacattgccg agcgcatcca ggaggccggc gcgggcctgc   960
gtagcctggc agagccgtgg gccgacacca ccacgccggc cggccgcatg gtgttgaccg  1020
tgttcgccgg cattgccgag ttcgagcgtt ccctaatcat cgaccgcacc cggagcgggc  1080
gcgaggccgc caaggcccga ggcgtgaagt ttggcccccg ccctaccctc accccggcac  1140
agatcgcgca cgcccgcgag ctgatcgacc aggaaggccg caccgtgaaa gaggcggctg  1200
cactgcttgg cgtgcatcgc tcgaccctgt accgcgcact tgagcgcagc gaggaagtga  1260
cgcccaccga ggccaggcgg cgcggtgcct tccgtgagga cgcattgacc gaggccgacg  1320
ccctggcggc cgccgagaat gaacgccaag aggaacaagc atgaaaccgc accaggacgg  1380
ccaggacgaa ccgttttttca ttaccgaaga gatcgaggcg gagatgatcg cggccgggta  1440
cgtgttcgag ccgccgcgc acgtctcaac cgtgcggctg catgaaatcc tggccggttt  1500
gtctgatgcc aagctggcgg cctggccggc cagcttggcc gctgaagaaa ccgagcgccg  1560
ccgtctaaaa aggtgatgtg tatttgagta aaacagcttg cgtcatgcgg tcgctgcgta  1620
tatgatgcga tgagtaaata aacaaatacg caaggggaac gcatgaaggt tatcgctgta  1680
cttaaccaga aaggcgggtc aggcaagacg accatcgcaa cccatctagc ccgcgccctg  1740
caactcgccg gggccgatgt tctgttagtc gattccgatc cccagggcag tgcccgcgat  1800
tgggcggccg tgcgggaaga tcaaccgcta accgttgtcg gcatcgaccg cccgacgatt  1860
gaccgcgacg tgaaggccat cggccggcgc gacttcgtag tgatcgacgg agcgccccag  1920
gcggcggact tggctgtgtc cgcgatcaag gcagccgact tcgtgctgat tccggtgcag  1980
ccaagccctt acgacatatg ggccaccgcc gacctggtgg agctggttaa gcagcgcatt  2040
gaggtcacgg atggaaggct acaagcggcc tttgtcgtgt cgcgggcgat caaaggcacg  2100
cgcatcggcg gtgaggttgc cgaggcgctg gccgggtacg agctgcccat tcttgagtcc  2160
cgtatcacgc agcgcgtgag ctacccaggc actgccgccg ccggcacaac cgttcttgaa  2220
tcagaacccg agggcgacgc tgcccgcgag gtccaggcgc tggccgctga aattaaatca  2280
aaactcattt gagttaatga ggtaaagaga aaatgagcaa agcacaaac acgctaagtg  2340
ccggccgtcc gagcgcacgc agcagcaagg ctgcaacgtt ggccagcctg cagacacgc   2400
cagccatgaa gcgggtcaac tttcagttgc cggcggagga tcacaccaag ctgaagatgt  2460
acgcggtacg ccaaggcaag accattaccg agctgctatc tgaatacatc gcgcagctac  2520
cagagtaaat gagcaaatga ataaatgagt agatgaattt tagcggctaa aggaggcggc  2580
atggaaaatc aagaacaacc aggcaccgac gccgtggaat gccccatgtg tggaggaacg  2640
```

```
ggcggttggc caggcgtaag cggctgggtt gtctgccggc cctgcaatgg cactggaacc    2700
cccaagcccg aggaatcggc gtgacggtcg caaaccatcc ggcccggtac aaatcggcgc    2760
ggcgctgggt gatgacctgg tggagaagtt gaaggccgcg caggccgccc agcggcaacg    2820
catcgaggca gaagcacgcc ccggtgaatc gtggcaagcg gccgctgatc gaatccgcaa    2880
agaatcccgg caaccgccgg cagccggtgc gccgtcgatt aggaagccgc caagggcga    2940 cgagcaacca gattttttcg ttccgatgct ctatgacgtg gcacccgcg atagtcgcag    3000 catcatggac gtggccgttt tccgtctgtc gaagcgtgac cgacgagctg gcgaggtgat    3060
ccgctacgag cttccagacg ggcacgtaga ggtttccgca gggccggccg gcatggccag    3120
tgtgtgggat tacgacctgg tactgatggc ggtttcccat ctaaccgaat ccatgaaccg    3180
ataccgggaa gggaagggag acaagcccgg ccgcgtgttc cgtccacacg ttgcggacgt    3240
actcaagttc tgccggcgag ccgatggcgg aaagcagaaa gacgacctgg tagaaacctg    3300
cattcggtta acaccacgc acgttgccat gcagcgtacg aagaaggcca agaacggccg    3360
cctggtgacg gtatccgagg gtgaagcctt gattagccgc tacaagatcg taagagcga    3420 aaccgggcgg ccggagtaca tcgagatcga gctagctgat tggatgtacc gcagatcac    3480 agaaggcaag aacccggacg tgctgacggt tcaccccgat tacttttga tcgatcccgg    3540 catcggccgt tttctctacc gcctggcacg ccgcgccgca ggcaaggcag aagccagatg    3600
gttgttcaag acgatctacg aacgcagtgg cagcgccgga gagttcaaga agttctgttt    3660
caccgtgcgc aagctgatcg ggtcaaatga cctgccggag tacgatttga aggaggaggc    3720
ggggcaggct ggcccgatcc tagtcatgcg ctaccgcaac ctgatcgagg gcgaagcatc    3780
cgccggttcc taatgtacgg agcagatgct agggcaaatt gccctagcag gggaaaaagg    3840
tcgaaaaggt ctcttttcctg tggatagcac gtacattggg aacccaaagc cgtacattgg    3900
gaaccggaac ccgtacattg ggaacccaaa ccgtacatt gggaaccggt cacacatgta    3960
agtgactgat ataaaagaga aaaaggcga ttttccgcc taaaactctt taaaacttat    4020
taaaactctt aaaacccgcc tggcctgtgc ataactgtct ggccagcgca cagccgaaga    4080
gctgcaaaaa gcgcctaccc ttcggtcgct gcgctcccta cgccccgccg cttcgcgtcg    4140
gcctatcgcg gccgctggcc gctcaaaaat ggctggccta cggccaggca atctaccagg    4200
gcgcggacaa gccgcgccgt cgccactcga ccgccggcgc ccacatcaag gcaccctgcc    4260
tcgcgcgttt cggtgatgac ggtgaaaacc tctgacacat gcagctcccg gagacggtca    4320
cagcttgtct gtaagcggat gccgggagca gacaagcccg tcagggcgcg tcagcgggtg    4380
ttggcgggtg tcggggcgca gccatgaccc agtcacgtag cgatagcgga gtgtatactg    4440
gcttaactat gcggcatcag agcagattgt actgagagtg caccatatgc ggtgtgaaat    4500
accgcacaga tgcgtaagga gaaaataccg catcaggcgc tcttccgctt cctcgctcac    4560
tgactcgctg cgctcggtcg ttcggctgcg gcgagcggta tcagctcact caaaggcggt    4620
aatacggtta tccacagaat caggggataa cgcaggaaag aacatgtgag caaaaggcca    4680
gcaaaaggcc aggaaccgta aaaaggccgc gttgctggcg ttttccata ggctccgccc    4740 ccctgacgag catcacaaaa atcgacgctc aagtcagagg tggcgaaacc cgacaggact    4800
ataaagatac caggcgtttc ccctggaag ctccctcgtg cgctctcctg ttccgaccct    4860
gccgcttacc ggatacctgt ccgcctttct cccttcggga agcgtggcgc tttctcatag    4920
ctcacgctgt aggtatctca gttcggtgta ggtcgttcgc tccaagctgg gctgtgtgca    4980
```

```
cgaaccccccc gttcagcccg accgctgcgc cttatccggt aactatcgtc ttgagtccaa    5040
cccggtaaga cacgacttat cgccactggc agcagccact ggtaacagga ttagcagagc    5100
gaggtatgta ggcggtgcta cagagttctt gaagtggtgg cctaactacg gctacactag    5160
aaggacagta tttggtatct gcgctctgct gaagccagtt accttcggaa aaagagttgg    5220
tagctcttga tccggcaaac aaaccaccgc tggtagcggt ggtttttttg tttgcaagca    5280
gcagattacg cgcagaaaaa aaggatctca agaagatcct ttgatctttt ctacggggtc    5340
tgacgctcag tggaacgaaa actcacgtta agggattttg gtcatgcatt ctaggtacta    5400
aaacaattca tccagtaaaa tataatattt tattttctcc caatcaggct tgatccccag    5460
taagtcaaaa aatagctcga catactgttc ttccccgata tcctccctga tcgaccggac    5520
gcagaaggca atgtcatacc acttgtccgc cctgccgctt ctcccaagat caataaagcc    5580
acttactttg ccatctttca caaagatgtt gctgtctccc aggtcgccgt gggaaaagac    5640
aagttcctct tcgggctttt ccgtctttaa aaaatcatac agctcgcgcg gatctttaaa    5700
tggagtgtct tcttcccagt tttcgcaatc cacatcggcc agatcgttat tcagtaagta    5760
atccaattcg gctaagcggc tgtctaagct attcgtatag gacaatccg atatgtcgat    5820 ggagtgaaag agcctgatgc actccgcata cagctcgata tcttttcag ggctttgttc    5880 atcttcatac tcttccgagc aaaggacgcc atcggcctca ctcatgagca gattgctcca    5940
gccatcatgc cgttcaaagt gcaggacctt tggaacaggc agctttcctt ccagccatag    6000
catcatgtcc ttttccgtt ccacatcata ggtggtccct ttataccggc tgtccgtcat    6060
ttttaaatat aggttttcat tttctcccac cagcttatat accttagcag agacattcc     6120 ttccgtatct tttacgcagc ggtatttttc gatcagtttt ttcaattccg gtgatattct    6180
cattttagcc atttattatt tccttcctct tttctacagt attaaagat accccaagaa     6240 gctaattata acaagacgaa ctccaattca ctgttccttg cattctaaaa ccttaaatac    6300
cagaaaacag cttttttcaaa gttgttttca aagttggcgt ataacatagt atcgacggag    6360
ccgattttga aaccgcggtg atcacaggca gcaacgctct gtcatcgtta caatcaacat    6420
gctaccctcc gcgagatcat ccgtgttcca aacccggcag cttagttgcc gttcttccga    6480
atagcatcgg taacatgagc aaagtctgcc gccttacaac ggctctcccg ctgacgccgt    6540
cccggactga tgggctgcct gtatcgagtg gtgattttgt gccgagctgc cggtcgggga    6600
gctgttggct ggctggtggc aggatatatt gtggtgtaaa caaattgacg cttagacaac    6660
ttaataacac attgcggacg ttttttaatgt actgaattaa cgccgaatta attcggggga    6720 tctggattttt agtactggat tttggttta ggaattagaa attttattga tagaagtatt    6780
ttacaaatac aaatacatac taagggtttc ttatatgctc aacacatgag cgaaaccca    6840 taggaaccct aattcccttta tctgggaact actcacacat tattatggag aaactcgagc    6900
ttgtcgatcg actctagcta gaggatcgat ccgaaccccca gagtcccgct cagaagaact    6960
cgtcaagaag gcgatagaag gcgatgcgct gcgaatcggg agcggcgata ccgtaaagca    7020
cgaggaagcg gtcagcccat tcgccgccaa gctcttcagc aatatcacgg gtagccaacg    7080
ctatgtcctg atagcggtcc gccacaccca gccggccaca gtcgatgaat ccagaaaagc    7140
ggccattttc caccatgata ttcggcaagc aggcatcgca atgggtcacg acgagatcat    7200
cgccgtcggg catgcgcgcc ttgagcctgg cgaacagttc ggctggcgcg agccctgat    7260 gctcttcgtc cagatcatcc tgatcgacaa gaccggcttc catccgagta cgtgctcgct   7320
cgatgcgatg tttcgcttgg tggtcgaatg ggcaggtagc cggatcaagc gtatgcagcc   7380
```

```
gccgcattgc atcagccatg atggatactt tctcggcagg agcaaggtga gatgacagga    7440
gatcctgccc cggcacttcg cccaatagca gccagtccct tcccgcttca gtgacaacgt    7500
cgagcacagc tgcgcaagga acgcccgtcg tggccagcca cgatagccgc gctgcctcgt    7560
cctgcagttc attcagggca ccggacaggt cggtcttgac aaaaagaacc gggcgcccct    7620
gcgctgacag ccggaacacg gcggcatcag agcagccgat tgtctgttgt gcccagtcat    7680
agccgaatag cctctccacc caagcggccg gagaacctgc gtgcaatcca tcttgttcaa    7740
tcatgcgaaa cgatccagat ccggtgcaga ttatttggat tgagagtgaa tatgagactc    7800
taattggata ccgaggggaa tttatggaac gtcagtggag cattttttgac aagaaatatt   7860
tgctagctga tagtgacctt aggcgacttt tgaacgcgca ataatggttt ctgacgtatg    7920
tgcttagctc attaaactcc agaaacccgc ggctgagtgg ctccttcaat cgttgcggtt    7980
ctgtcagttc caaacgtaaa acggcttgtc ccgcgtcatc ggcgggggtc ataacgtgac    8040
tcccttaatt ctccgctcat gatcagattg tcgtttcccg ccttcagttt ccaagcttgg    8100
cactggccgt cgttttacaa cgtcgtgact gggaaaaccc tggcgttacc caacttaatc    8160
gccttgcagc acatcccccct ttcgccagct ggcgtaatag cgaagaggcc cgcaccgatc   8220
gcccttccca acagttgcgc agcctgaatg gcgaatgcta gagcagcttg agcttggatc    8280
agattgtcgt ttcccgcctt cagtttagct tcatggagtc aaagattcaa atagaggacc    8340
taacagaact cgccgtaaag actggcgaac agttcataca gagtctctta cgactcaatg    8400
acaagaagaa aatcttcgtc aacatggtgg agcacgacac acttgtctac tccaaaaata    8460
tcaaagatac agtctcagaa gaccaaaggg caattgagac ttttcaacaa agggtaatat    8520
ccggaaacct cctcggattc cattgcccag ctatctgtca ctttattgtg aagatagtgg    8580
aaaaggaagg tggctcctac aaatgccatc attgcgataa aggaaaggcc atcgttgaag    8640
atgcctctgc cgacagtggt cccaaagatg gacccccacc cacgaggagc atcgtggaaa    8700
aagaagacgt tccaaccacg tcttcaaagc aagtggattg atgtgatatc tccactgacg    8760
taagggatga cgcacaatcc cactatcctt cgcaagaccc ttcctctata taaggaagtt    8820
catttcattt ggagagaaca cggggggactc ttgaacatgt ctgatcagac cgataccacc   8880
cagaccactc ctgccgagaa ggctcctcca aaagaaatta tcaggggtag aatgcctatc    8940
gcagttgtag ctcttgcaag attcggctct cagtcaacta ccacaactaa ggctgcaggt    9000
aaatttctag ttttttctcct tcatttttctt ggttaggacc cttttctctt tttatttttt   9060
tgagcttcga tctgttttta aactgatcta tttttttaatt gattggttat ggtgtaaata   9120
ttacatagct ttaactgata atctgattac tttatttcgt gtgtaattga ttaattctgc    9180
agccgatgct cttggcacta cagttggtaa gattgatgac atcagaaaga acaggaactt    9240
cgcttacgtt acagcagatt tcaagcctac cgaagcccag aaggctgatg catcgagtg    9300
gcttaagaga catccagttg gtgctgatgc cttgattgaa gagcttcaga acctccctgt    9360
tgctactgcc gaagagtctg ctgcattcga gcaggttagg gcatcagcta gaggccagaa    9420
cgccaagact gctgagggag aagttgctca ggctggcggc ggaaatagaa ggaagaaaaa    9480
ggaaaagcct gccgaagctg gtgaggtgca gaaccctcca gcagctgatg gcgactctct    9540
tttgtcataa tctagactag t                                              9561

<210> SEQ ID NO 4
<211> LENGTH: 9851
<212> TYPE: DNA
```

<213> ORGANISM: Artificial Sequence
<220> FEATURE:
<223> OTHER INFORMATION: plasmid

<400> SEQUENCE: 4

```
tgctacagag ttcttgaagt ggtggcctaa ctacggctac actagaagga cagtatttgg      60
tatctgcgct ctgctgaagc cagttacctt cggaaaaaga gttggtagct cttgatccgg     120
caaacaaacc accgctggta gcggtggttt ttttgtttgc aagcagcaga ttacgcgcag     180
aaaaaaagga tctcaagaag atcctttgat cttttctacg gggtctgacg ctcagtggaa     240
cgaaaactca cgttaaggga ttttggtcat gcatgatata tctcccaatt tgtgtagggc     300
ttattatgca cgcttaaaaa taataaaagc agacttgacc tgatagtttg gctgtgagca     360
attatgtgct tagtgcatct aatcgcttga gttaacgccg gcgaagcggc gtcggcttga     420
acgaatttct agctagacat tatttgccga ctaccttggt gatctcgcct ttcacgtagt     480
ggacaaattc ttccaactga tctgcgcgcg aggccaagcg atcttcttct tgtccaagat     540
aagcctgtct agcttcaagt atgacgggct gatactgggc cggcaggcgc tccattgccc     600
agtcggcagc gacatccttc ggcgcgattt tgccggttac tgcgctgtac caaatgcggg     660
acaacgtaag cactacattt cgctcatcgc cagcccagtc gggcggcgag ttccatagcg     720
ttaaggtttc atttagcgcc tcaaatagat cctgttcagg aaccggatca agagttcct      780
ccgccgctgg acctaccaag gcaacgctat gttctcttgc ttttgtcagc aagatagcca     840
gatcaatgtc gatcgtggct ggctcgaaga tacctgcaag aatgtcattg cgctgccatt     900
ctccaaattg cagttcgcgc ttagctggat aacgccacgg aatgatgtcg tcgtgcacaa     960
caatggtgac ttctacagcg cggagaatct cgctctctcc aggggaagcc gaagtttcca    1020
aaaggtcgtt gatcaaagct cgccgcgttg tttcatcaag ccttacggtc accgtaacca    1080
gcaaatcaat atcactgtgt ggcttcaggc cgccatccac tgcggagccg tacaaatgta    1140
cggccagcaa cgtcggttcg agatggcgct cgatgacgcc aactacctct gatagttgag    1200
tcgatacttc ggcgatcacc gcttccccca tgatgtttaa cttttgtttt gggcgactgc    1260
cctgctgcgt aacatcgttg ctgctccata acatcaaaca tcgacccacg cgtaacgcg     1320
cttgctgctt ggatgcccga ggcatagact gtaccccaaa aaacatgtc ataacaagaa     1380
gccatgaaaa ccgccactgc gccgttacca ccgctgcgtt cggtcaaggt tctgaccag     1440
ttgcgtgacg gcagttacgc tacttgcatt acagcttacg aaccgaacga ggcttatgtc    1500
cactgggttc gtgcccgaat tgatcacagg cagcaacgct ctgtcatccg cggtgatcac    1560
aggcagcaac gctctgtcat cgttacaatc aacatgctac cctccgcgag atcatccgtg    1620
tttcaaaccc ggcagcttag ttgccgttct tccgaatagc atcggtaaca tgagcaaagt    1680
ctgccgcctt acaacggctc tcccgctgac gccgtccggg actgatgggc tgcctgtatc    1740
gagtggtgat tttgtgccga gctgccggtc ggggagctgt tggctggctg gtggcaggat    1800
atattgtggt gtaaacaaat tgacgcttag acaacttaat aacacattgc ggacgttttt    1860
aatgtactga attaacgccg aattaattcg ggggatctgg attttagtac tggattttgg    1920
ttttaggaat tagaaatttt attgatagaa gtattttaca aatacaaata catactaagg    1980
gtttcttata tgctcaacac atgagcgaaa ccctatagga accctaattc ccttatctgg    2040
gaactactca cacattatta tggagaaact cgagcttgtc gatcgactct agctagagga    2100
tcgatccgaa ccccagagtc ccgctcagaa gaactcgtca agaaggcgat agaaggcgat    2160
gcgctgcgaa tcgggagcgg cgataccgta aagcacgagg aagcggtcag cccattcgcc    2220
```

-continued

```
gccaagctct tcagcaatat cacgggtagc caacgctatg tcctgatagc ggtccgccac    2280
acccagccgg ccacagtcga tgaatccaga aaagcggcca ttttccacca tgatattcgg    2340
caagcaggca tcgccatggg tcacgacgag atcatcgccg tcgggcatgc gcgccttgag    2400
cctggcgaac agttcggctg gcgcgagccc ctgatgctct tcgtccagat catcctgatc    2460
gacaagaccg gcttccatcc gagtacgtgc tcgctcgatg cgatgtttcg cttggtggtc    2520
gaatgggcag tagccggat caagcgtatg cagccgccgc attgcatcag ccatgatgga    2580
tactttctcg gcaggagcaa ggtgagatga caggagatcc tgccccggca cttcgcccaa    2640
tagcagccag tcccttcccg cttcagtgac aacgtcgagc acagctgcgc aaggaacgcc    2700
cgtcgtggcc agccacgata gccgcgctgc ctcgtcctgc agttcattca gggcaccgga    2760
caggtcggtc ttgacaaaaa gaaccgggcg ccctgcgct gacagccgga acacggcggc    2820
atcagagcag ccgattgtct gttgtgccca gtcatagccg aatagcctct ccacccaagc    2880
ggccggagaa cctgcgtgca atccatcttg ttcaatcatg cgaaacgatc cagatccggt    2940
gcagattatt tggattgaga gtgaatatga gactctaatt ggataccgag gggaatttat    3000
ggaacgtcag tggagcattt ttgacaagaa atatttgcta gctgatagtg accttaggcg    3060
acttttgaac gcgcaataat ggtttctgac gtatgtgctt agctcattaa actccagaaa    3120
cccgcggctg agtggctcct tcaatcgttg cggttctgtc agttccaaac gtaaaacggc    3180
ttgtcccgcg tcatcggcgg gggtcataac gtgactccct taattctccg ctcatgatca    3240
gattgtcgtt tcccgccttc agtttccaag cttggcactg gccgtcgttt tacaacgtcg    3300
tgactgggaa aaccctggcg ttacccaact taatcgcctt gcagcacatc ccccctttcgc    3360 cagctggcgt aatagcgaag aggcccgcac cgatcgccct tcccaacagt tgcgcagcct    3420
gaatggcgaa tgctagagca gcttgagctt ggatcagatt gtcgtttccc gccttcagtt    3480
tagcttcatg gagtcaaaga ttcaaataga ggacctaaca gaactcgccg taaagactgg    3540
cgaacagttc atacagagtc tcttacgact caatgacaag aagaaaatct tcgtcaacat    3600
ggtggagcac gacacacttg tctactccaa aaatatcaaa gatacagtct cagaagacca    3660
aagggcaatt gagacttttc aacaaagggt aatatccgga aacctcctcg gattccattg    3720
cccagctatc tgtcacttta ttgtgaagat agtggaaaag gaaggtggct cctacaaatg    3780
ccatcattgc gataaaggaa aggccatcgt tgaagatgcc tctgccgaca gtggtcccaa    3840
agatggaccc ccacccacga ggagcatcgt ggaaaaagaa gacgttccaa ccacgtcttc    3900
aaagcaagtg gattgatgtg atatctccac tgacgtaagg gatgacgcac aatcccacta    3960
tccttcgcaa gacccttcct ctatataagg aagttcattt catttggaga gaacacgggg    4020
gactcttgaa catgtctgat cagaccgata ccacccagac cactcctgcc gagaaggctc    4080
ctccaaaaga aattatcagg ggtagaatgc ctatcgcagt tgtagctctt gcaagattcg    4140
gctctcagtc aactaccaca actaaggctg caggtaaatt tctagttttt ctccttcatt    4200
ttcttggtta ggaccctttt ctcttttat ttttttgagc ttcgatctgt ttttaaactg    4260
atctattttt taattgattg ttatggtgt aaatattaca tagctttaac tgataatctg    4320
attactttat ttcgtgtgta attgattaat tctgcagccg atgctcttgg cactacagtt    4380
ggtaagattg atgacatcag aaagaacagg aacttcgctt acgttacagc agatttcaag    4440
cctaccgaag cccagaaggc tgatggcatc gagtggctta agagacatcc agttggtgct    4500
gatgccttga ttgaagagct tcagaacctc cctgttgcta ctgccgaaga gtctgctgca    4560
```

```
ttcgagcagg ttagggcatc agctagaggc cagaacgcca agactgctga gggagaagtt    4620
gctcaggctg gcggcggaaa tagaaggaag aaaaaggaaa agcctgccga agctggtgag    4680
gtgcagaacc ctccagcagc tgatggcgac tctcttttgt cataatctag actagtgtta    4740
acgctagcca ccaccaccac caccacgtgt gaattacagg tgaccagctc gaatttcccc    4800
gatcgttcaa acatttggca ataaagtttc ttaagattga atcctgttgc cggtcttgcg    4860
atgattatca tataatttct gttgaattac gttaagcatg taataattaa catgtaatgc    4920
atgacgttat ttatgagatg gttttttatg attagagtcc cgcaattata catttaatac    4980
gcgatagaaa acaaaatata gcgcgcaaac taggataaat tatcgcgcgc ggtgtcatct    5040
atgttactag atcgggaatt aaactatcag tgtttgacag gatatattgg cgggtaaacc    5100
taagagaaaa gagcgtttat tagaataacg gatatttaaa agggcgtgaa aaggtttatc    5160
cgttcgtcca tttgtatgtg catgccaacc acagggttcc cctcgggatc aaagtacttt    5220
gatccaaccc ctccgctgct atagtgcagt cggcttctga cgttcagtgc agccgtcttc    5280
tgaaaacgac atgtcgcaca agtcctaagt tacgcgacag gctgccgccc tgcccttttc    5340
ctggcgtttt cttgtcgcgt gttttagtcg cataaagtag aatacttgcg actagaaccg    5400
gagacattac gccatgaaca agagcgccgc cgctggcctg ctgggctatg cccgcgtcag    5460
caccgacgac caggacttga ccaaccaacg ggccgaactg cacgcggccg gctgcaccaa    5520
gctgttttcc gagaagatca ccggcaccag gcgcgaccgc ccggagctgg ccaggatgct    5580
tgaccaccta cgccctggcg acgttgtgac agtgaccagg ctagaccgcc tggcccgcag    5640
cacccgcgac ctactggaca ttgccgagcg catccaggag gccggcgcgg gcctgcgtag    5700
cctggcagag ccgtgggccg acaccaccac gccggccggc cgcatggtgt tgaccgtgtt    5760
cgccggcatt gccgagttcg agcgttccct aatcatcgac cgcacccgga gcgggcgcga    5820
ggccgccaag gcccgaggcg tgaagtttgg cccccgccct accctcaccc cggcacagat    5880
cgcgcacgcc cgcgagctga tcgaccagga aggccgcacc gtgaaagagg cggctgcact    5940
gcttggcgtg catcgctcga ccctgtaccg cgcacttgag cgcagcgagg aagtgacgcc    6000
caccgaggcc aggcggcgcg tgccttccg tgaggacgca ttgaccgagg ccgacgccct    6060
ggcggccgcc gagaatgaac gccaagagga acaagcatga aaccgcacca ggacggccag    6120
gacgaaccgt ttttcattac cgaagagatc gaggcggaga tgatcgcggc cgggtacgtg    6180
ttcgagccgc ccgcgcacgt ctcaaccgtg cggctgcatg aaatcctggc cggtttgtct    6240
gatgccaagc tggcggcctg gccggccagc ttggccgctg aagaaaccga gcgccgccgt    6300
ctaaaaaggt gatgtgtatt tgagtaaaac agcttgcgtc atgcggtcgc tgcgtatatg    6360
atgcgatgag taaataaaca aatacgcaag gggaacgcat gaaggttatc gctgtactta    6420
accagaaagg cgggtcaggc aagacgacca tcgcaaccca tctagcccgc gccctgcaac    6480
tcgccggggc cgatgttctg ttagtcgatt ccgatcccca gggcagtgcc cgcgattggg    6540
cggccgtgcg ggaagatcaa ccgctaaccg ttgtcggcat cgaccgcccg acgattgacc    6600
gcgacgtgaa ggccatcggc cggcgcgact cgtagtgat cgacggagcg ccccaggcgg    6660
cggacttggc tgtgtccgcg atcaaggcag ccgacttcgt gctgattccg gtgcagccaa    6720
gcccttacga catatgggcc accgccgacc tggtggagct ggttaagcag cgcattgagg    6780
tcacggatgg aaggctacaa gcggcctttg tcgtgtcgcg ggcgatcaaa ggcacgcgca    6840
tcggcggtga ggttgccgag gcgctggccg ggtacgagct gcccattctt gagtcccgta    6900
tcacgcagcg cgtgagctac ccaggcactg ccgccgccgg cacaaccgtt cttgaatcag    6960
```

```
aacccgaggg cgacgctgcc cgcgaggtcc aggcgctggc cgctgaaatt aaatcaaaac   7020
tcatttgagt taatgaggta aagagaaaat gagcaaaagc acaaacacgc taagtgccgg   7080
ccgtccgagc gcacgcagca gcaaggctgc aacgttggcc agcctggcag acacgccagc   7140
catgaagcgg gtcaactttc agttgccggc ggaggatcac accaagctga agatgtacgc   7200
ggtacgccaa ggcaagacca ttaccgagct gctatctgaa tacatcgcgc agctaccaga   7260
gtaaatgagc aaatgaataa atgagtagat gaattttagc ggctaaagga ggcggcatgg   7320
aaaatcaaga acaaccaggc accgacgccg tggaatgccc catgtgtgga ggaacgggcg   7380
gttggccagg cgtaagcggc tgggttgtct gccggccctg caatggcact ggaaccccca   7440
agcccgagga atcggcgtga cggtcgcaaa ccatccggcc cggtacaaat cggcgcggcg   7500
ctgggtgatg acctggtgga gaagttgaag gccgcgcagg ccgcccagcg gcaacgcatc   7560
gaggcagaag cacgccccgg tgaatcgtgg caagcggccg ctgatcgaat ccgcaaagaa   7620
tcccggcaac cgccggcagc cggtgcgccg tcgattagga agccgcccaa gggcgacgag   7680
caaccagatt ttttcgttcc gatgctctat gacgtgggca cccgcgatag tcgcagcatc   7740
atggacgtgg ccgttttccg tctgtcgaag cgtgaccgac gagctggcga ggtgatccgc   7800
tacgagcttc cagacgggca cgtagaggtt tccgcagggc cggccggcat ggccagtgtg   7860
tgggattacg acctggtact gatggcggtt cccatctaa ccgaatccat gaaccgatac   7920
cgggaaggga agggagacaa gcccggccgc gtgttccgtc cacacgttgc ggacgtactc   7980
aagttctgcc ggcgagccga tggcggaaag cagaaagacg acctggtaga aacctgcatt   8040
cggttaaaca ccacgcacgt tgccatgcag cgtacgaaga aggccaagaa cggccgcctg   8100
gtgacggtat ccgagggtga agccttgatt agccgctaca agatcgtaaa gagcgaaacc   8160
gggcggccgg agtacatcga gatcgagcta gctgattgga tgtaccgcga gatcacagaa   8220
ggcaagaacc cggacgtgct gacggttcac cccgattact ttttgatcga tcccggcatc   8280 gccgttttc tctaccgcct ggcacgccgc gccgcaggca aggcagaagc cagatggttg   8340
ttcaagacga tctacgaacg cagtggcagc gccggagagt tcaagaagtt ctgtttcacc   8400
gtgcgcaagc tgatcgggtc aaatgacctg ccggagtacg atttgaagga ggaggcgggg   8460
caggctggcc cgatcctagt catgcgctac cgcaacctga tcgagggcga agcatccgcc   8520
ggttcctaat gtacggagca gatgctaggg caaattgccc tagcagggga aaaggtcga   8580 aaaggtctct ttcctgtgga tagcacgtac attgggaacc caaagccgta cattgggaac   8640
cggaacccgt acattgggaa cccaaagccg tacattggga accggtcaca catgtaagtg   8700
actgatataa aagagaaaaa aggcgatttt ccgcctaaaa ctctttaaaa acttattaaa   8760
actcttaaaa cccgctggc ctgtgcataa ctgtctggcc agcgcacagc cgaagagctg   8820
caaaaagcgc ctaccttcg gtcgctgcgc tccctacgcc ccgccgcttc gcgtcggcct   8880
atcgcggccg ctgccgctc aaaaatggct ggcctacggc caggcaatct accagggcgc   8940
ggacaagccg cgccgtcgcc actcgaccgc cggcgcccac atcaaggcac cctgcctcgc   9000
gcgtttcggt gatgacggtg aaaacctctg acacatgcag ctcccggaga cggtcacagc   9060
ttgtctgtaa gcggatgccg ggagcagaca agcccgtcag ggcgcgtcag cgggtgttgg   9120
cgggtgtcgg ggcgcagcca tgacccagtc acgtagcgat agcggagtgt atactggctt   9180
aactatgcgg catcagagca gattgtactg agagtgcacc atatgcggtg tgaaataccg   9240
cacagatgcg taaggagaaa ataccgcatc aggcgctctt ccgcttcctc gctcactgac   9300
```

```
tcgctgcgct cggtcgttcg gctgcggcga gcggtatcag ctcactcaaa ggcggtaata    9360
cggttatcca cagaatcagg ggataacgca ggaaagaaca tgtgagcaaa aggccagcaa    9420
aaggccagga accgtaaaaa ggccgcgttg ctggcgtttt tccataggct ccgcccccct    9480
gacgagcatc acaaaaatcg acgctcaagt cagaggtggc gaaacccgac aggactataa    9540
agataccagg cgtttccccc tggaagctcc ctcgtgcgct ctcctgttcc gaccctgccg    9600
cttaccggat acctgtccgc ctttctccct cgggaagcg tggcgctttc tcatagctca     9660
cgctgtaggt atctcagttc ggtgtaggtc gttcgctcca agctgggctg tgtgcacgaa    9720
ccccccgttc agcccgaccg ctgcgcctta tccggtaact atcgtcttga gtccaacccg    9780
gtaagacacg acttatcgcc actggcagca gccactggta acaggattag cagagcgagg    9840
tatgtaggcg g                                                         9851
```